(12) United States Patent
Eldar et al.

(10) Patent No.: US 11,883,240 B2
(45) Date of Patent: Jan. 30, 2024

(54) SPARSE CONVOLUTIONAL BEAMFORMING FOR ULTRASOUND IMAGING

(71) Applicants: Yonina C. Eldar, Rehovot (IL); Regev Cohen, Afula (IL)

(72) Inventors: Yonina C. Eldar, Rehovot (IL); Regev Cohen, Afula (IL)

(*) Notice: Subject to any disclaimer, the term of this patent is extended or adjusted under 35 U.S.C. 154(b) by 0 days.

(21) Appl. No.: 17/047,265

(22) PCT Filed: Apr. 15, 2019

(86) PCT No.: PCT/IL2019/050428
§ 371 (c)(1),
(2) Date: Oct. 13, 2020

(87) PCT Pub. No.: WO2019/202593
PCT Pub. Date: Oct. 24, 2019

(65) Prior Publication Data
US 2021/0212666 A1    Jul. 15, 2021

Related U.S. Application Data

(60) Provisional application No. 62/657,846, filed on Apr. 15, 2018.

(51) Int. Cl.
| | |
|---|---|
| *A61B 8/08* | (2006.01) |
| *G01S 15/89* | (2006.01) |
| *A61B 8/00* | (2006.01) |
| *G01S 7/52* | (2006.01) |

(52) U.S. Cl.
CPC ........ *A61B 8/5207* (2013.01); *G01S 15/8915* (2013.01); *A61B 8/4483* (2013.01); *G01S 7/52047* (2013.01)

(58) Field of Classification Search
CPC . A61B 8/5207; A61B 8/4483; G01S 15/8915; G01S 7/52047
See application file for complete search history.

(56) References Cited

U.S. PATENT DOCUMENTS

| 5,891,038 A * | 4/1999 | Seyed-Bolorforosh ..................... G01S 15/108 600/447 |
| 2005/0100127 A1* | 5/2005 | Zhao .................... A61B 6/4085 378/19 |

(Continued)

FOREIGN PATENT DOCUMENTS

| EP | 1046928 B1 | 10/2000 |
| KR | 20140057887 A * | 5/2014 |

(Continued)

OTHER PUBLICATIONS

PCT Search Report and Written Opinion for International Application No. PCT/IL2019/050428 dated Aug. 8, 2019, 16 pp.

(Continued)

*Primary Examiner* — Isam A Alsomiri
*Assistant Examiner* — Abdallah Abulaban
(74) *Attorney, Agent, or Firm* — The Roy Gross Law Firm, LLC; Roy Gross

(57) ABSTRACT

A method including receiving from multiple transducers respective signals comprising reflections of a transmitted signal from a target; processing the received signals to derive a beamformed signal, based, at least in part, on: (i) computing a specified value associated with each of the received signals, (ii) performing a convolution on all of the specified values, (iii) calculating a weighted sum of the results of the convolution, to derive the beamformed signal; and reconstructing an image of the target, based on the beamformed signal.

16 Claims, 23 Drawing Sheets

(56) References Cited

U.S. PATENT DOCUMENTS

| | | | |
|---|---|---|---|
| 2015/0265250 A1 | 9/2015 | Madore | |
| 2016/0249879 A1* | 9/2016 | Mauldin, Jr. | ........ A61B 8/5223 600/437 |
| 2017/0100097 A1* | 4/2017 | Owen | ................. G01S 15/8927 |
| 2019/0216430 A1* | 7/2019 | Hoctor | ................. G01S 15/8984 |

FOREIGN PATENT DOCUMENTS

| | | |
|---|---|---|
| KR | 20140057887 A * | 5/2014 |
| WO | 20130188707 A1 | 12/2013 |

OTHER PUBLICATIONS

A. Fenster and J. C. Lacefield, Ultrasound Imaging and Therapy, CRC Press, 2015.

Morten Fischer Rasmussen, Thomas Lehrmann Christiansen, Erik Vilain Thomsen, and Jørgen Arendt Jensen, "3-D imaging using row-column-addressed arrays with integrated apodization—Part I: Apodization design and line element beamforming", IEEE Transactions on Ultrasonics, Ferroelectrics, and Frequency Control, 62(5):947-958, 2015.

Jørgen Arendt Jensen and Niels Bruun Svendsen, "Calculation of pressure fields from arbitrarily shaped, apodized, and excited ultrasound transducers", IEEE Transactions on Ultrasonics, Ferroelectrics, and Frequency Control, 39(2):262-267, 1992.

PCT Preliminary Report on Patentability for International Application No. PCT/IL2019/050428 dated Oct. 20, 2020, 5 pp.

* cited by examiner

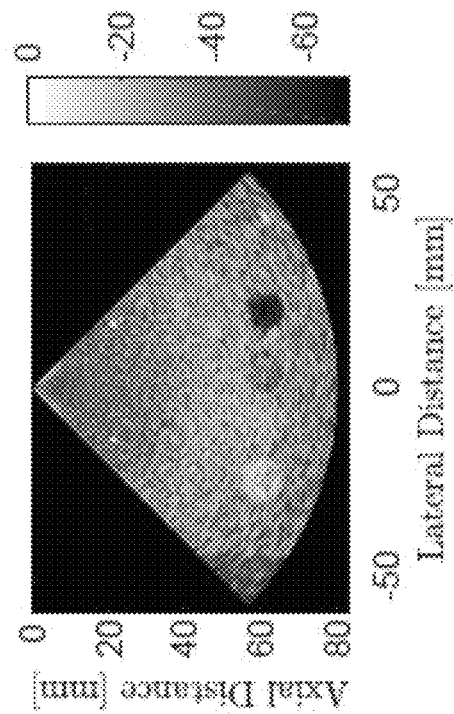
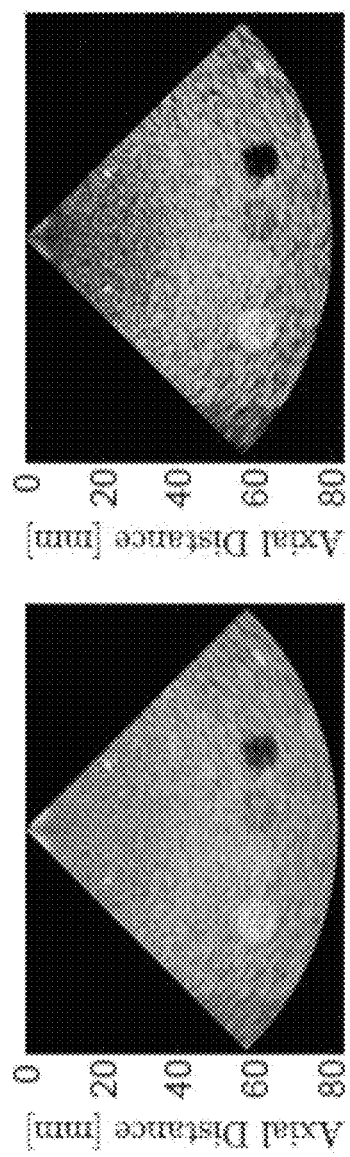
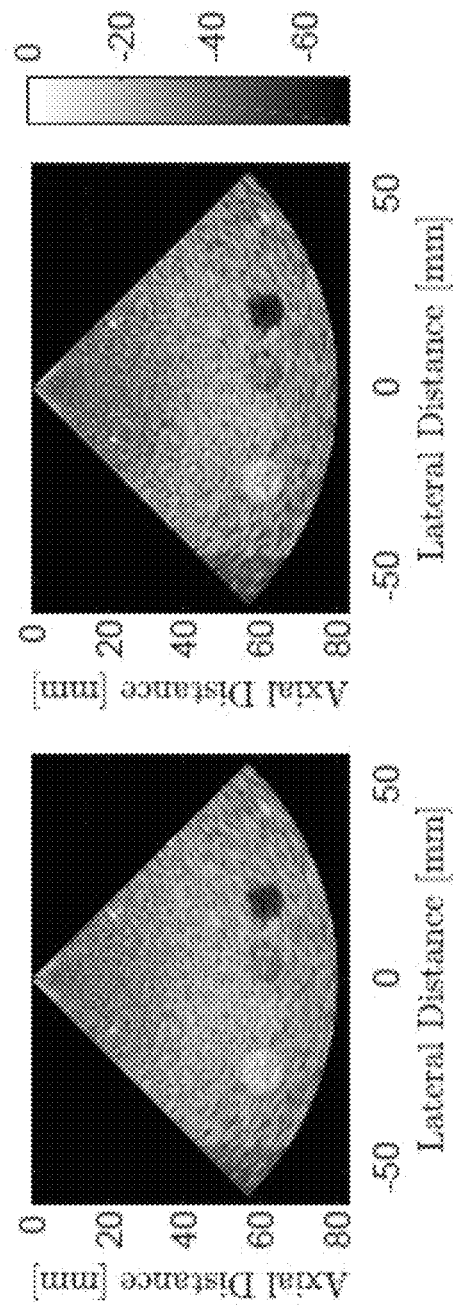
FIG. 12A
FIG. 12B
FIG. 12C
FIG. 12D

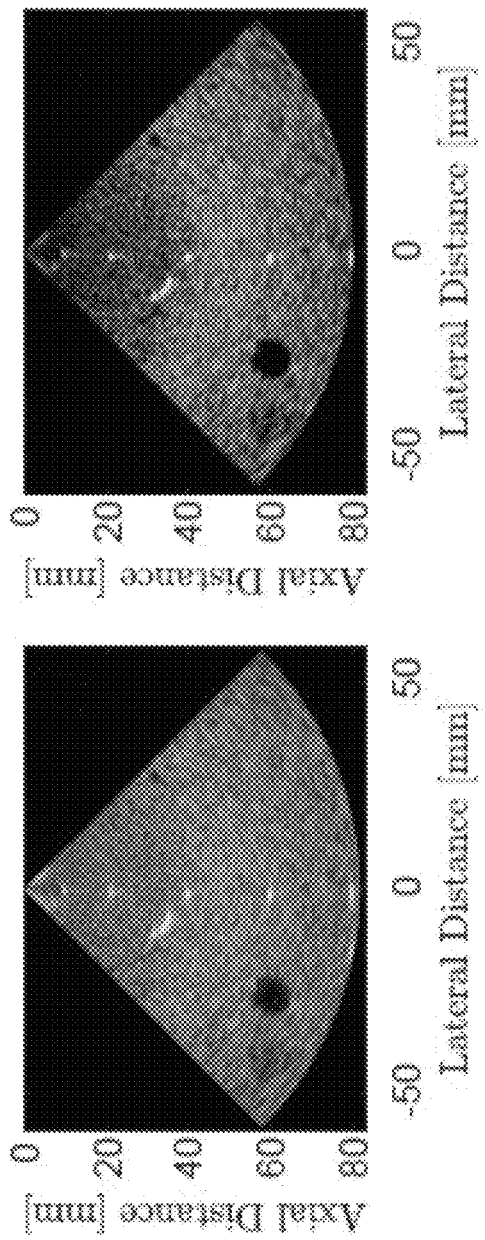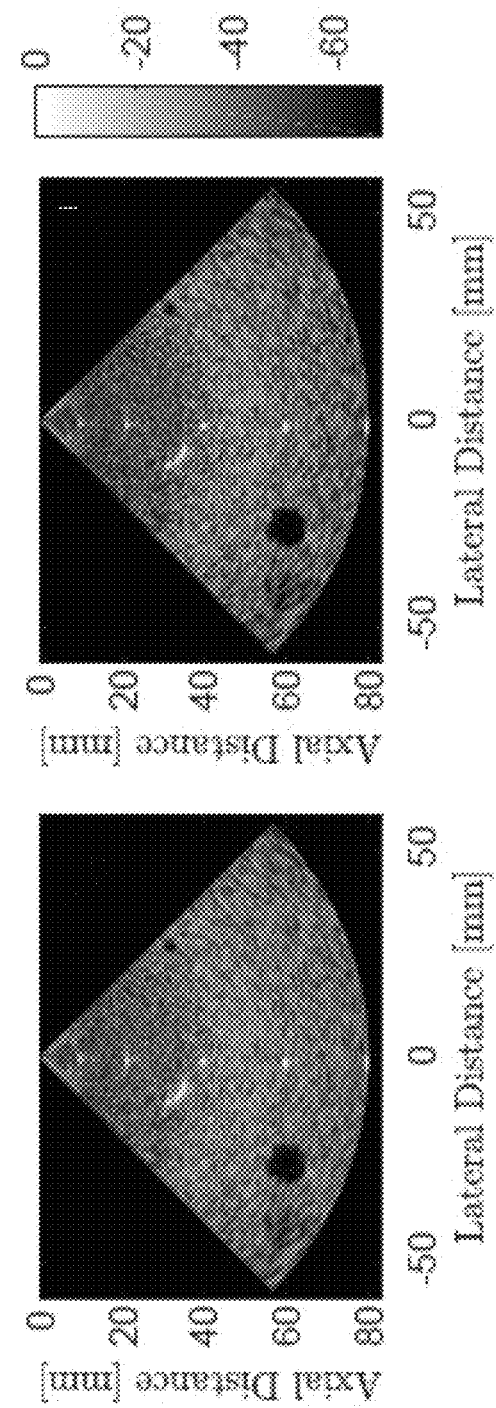
FIG. 14A    FIG. 14B    FIG. 14C    FIG. 14D

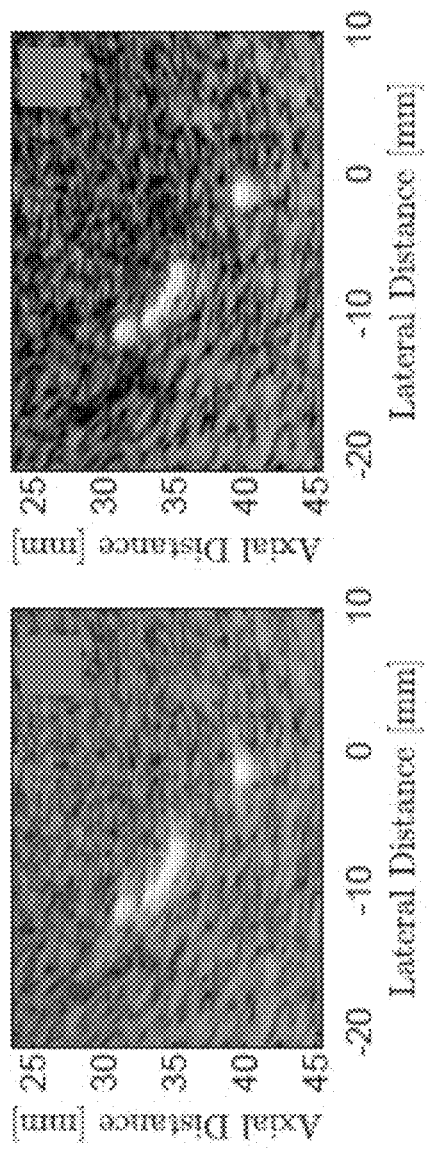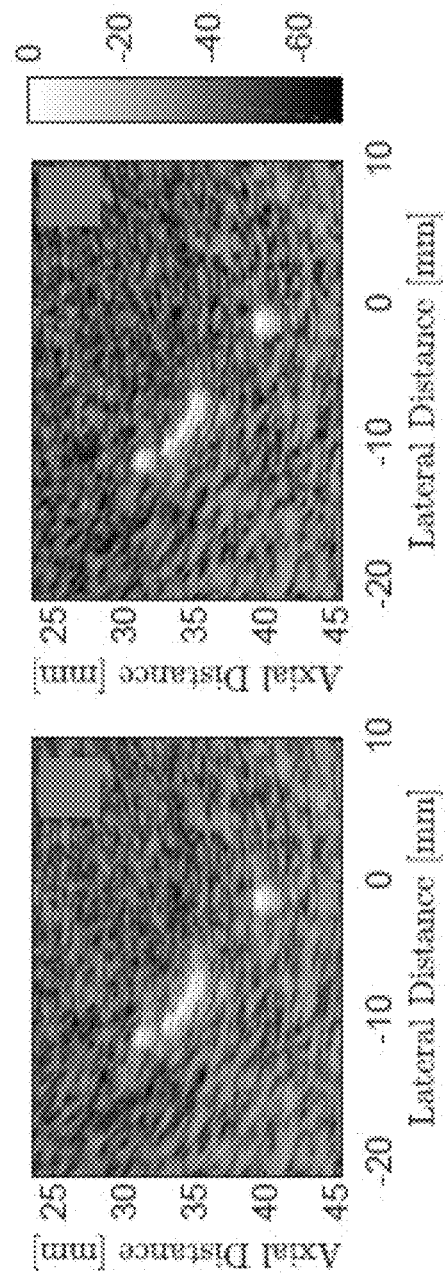

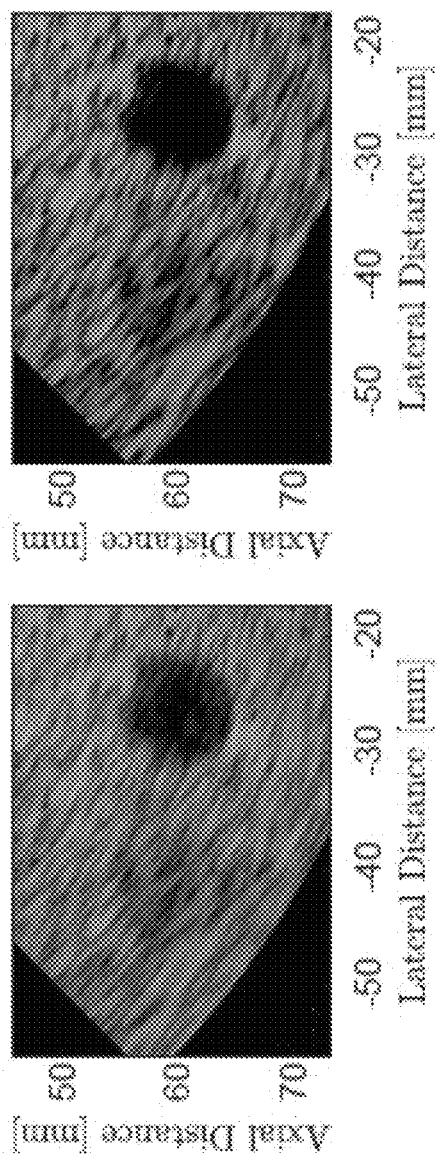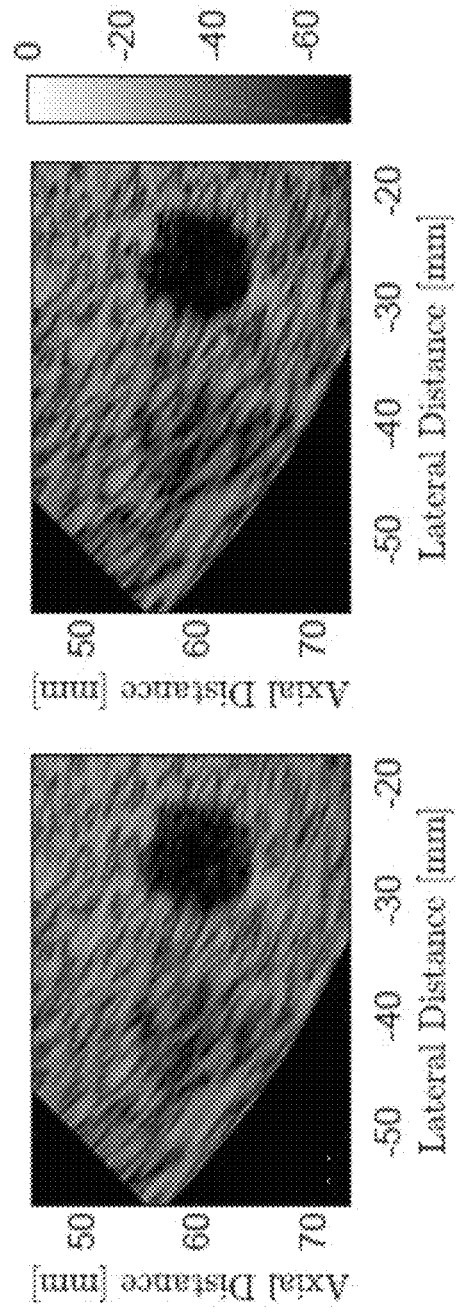
FIG. 16A  FIG. 16B  FIG. 16C  FIG. 16D

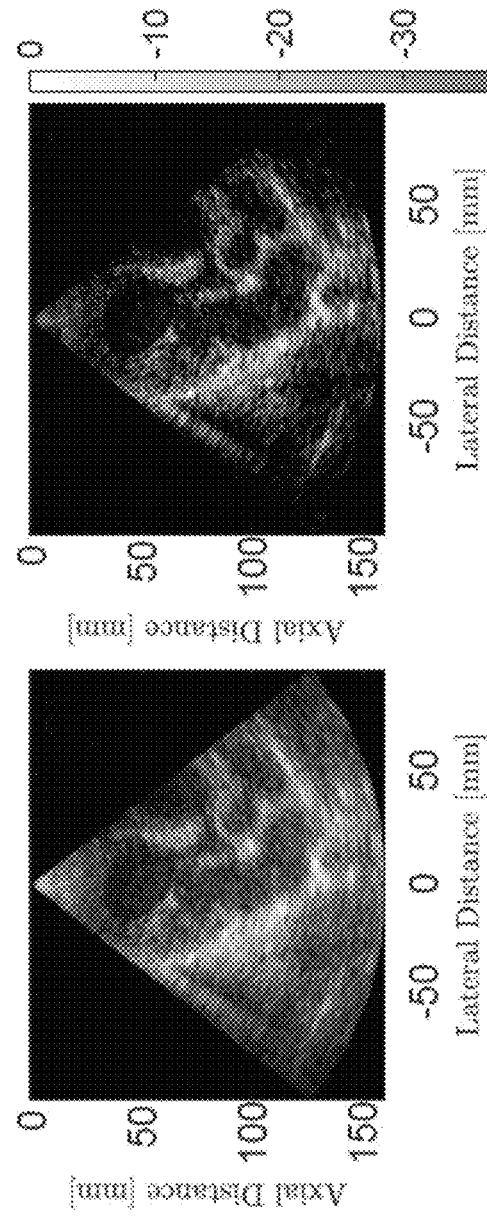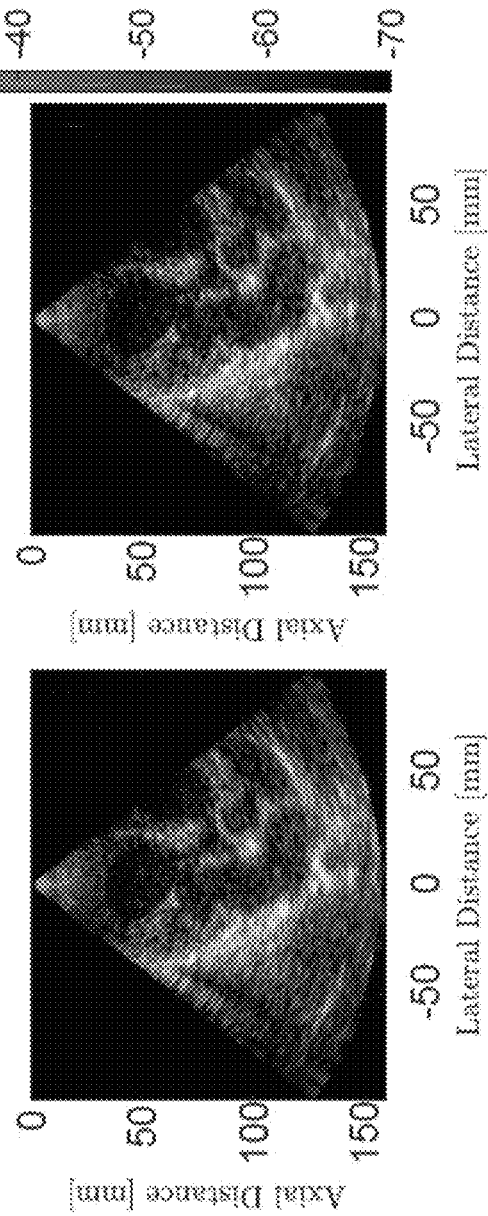
FIG. 17A  FIG. 17B  FIG. 17C  FIG. 17D

SPARSE CONVOLUTIONAL BEAMFORMING FOR ULTRASOUND IMAGING

CROSS-REFERENCE TO RELATED APPLICATIONS

This application is a National Phase of PCT Patent Application No. PCT/IL2019/050428 having International filing date of Apr. 5, 2019, which claims the benefit of priority of U.S. Provisional Patent Application No. 62/657, 846 filed Apr. 15, 2018, the contents of which are incorporated herein by reference in their entirety.

BACKGROUND

The invention relates to the field of ultrasound imaging.

Ultrasound imaging is one of the most common medical imaging modalities, allowing for non-invasive investigation of anatomical structures and blood flow. Cardiac, abdominal, fetal and breast imaging are some of the applications where it is extensively used as a diagnostic tool.

The standard technique used by commercial medical ultrasound systems to form B-mode images is delay and sum (DAS) beamforming. However, DAS often results in limited image resolution and contrast, which are governed by the center frequency and the aperture size of the ultrasound transducer. Increasing the number of array elements may lead to improved resolution, however, it also increases the data size and system costs due to the receive electronics required for each element. Therefore, reducing the number of receiving channels while producing high quality images is of great importance.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in an embodiment, a method comprising: receiving from multiple transducers respective signals comprising reflections of a transmitted signal from a target; processing said signals to derive a beamformed signal, based, at least in part, on: (i) computing a specified value associated with each of said signals, (ii) performing a convolution on all said specified values, and (iii) calculating a weighted sum of the results of said convolution, to derive said beamformed signal; and reconstructing an image of said target, based on said beamformed signal.

There is also provided, in an embodiment, a system comprising: at least one hardware processor; and a non-transitory computer-readable storage medium having stored thereon program instructions, the program instructions executable by the at least one hardware processor to: receive from multiple transducers respective signals comprising reflections of a transmitted signal from a target; process said signals to derive a beamformed signal, based, at least in part, on: (i) computing a specified value associated with each of said signals, (ii) performing a convolution on all said specified values, and (iii) calculating a weighted sum of the results of said convolution, to derive said beamformed signal; and reconstruct an image of said target, based on said beamformed signal.

There is further provided, in an embodiment, a computer program product comprising a non-transitory computer-readable storage medium having program instructions embodied therewith, the program instructions executable by at least one hardware processor to: receive from multiple transducers respective signals comprising reflections of a transmitted signal from a target; process said signals to derive a beamformed signal, based, at least in part, on: (i) computing a specified value associated with each of said signals, (ii) performing a convolution on all said specified values, and (iii) calculating a weighted sum of the results of said convolution, to derive said beamformed signal; and reconstruct an image of said target, based on said beamformed signal.

In some embodiments, said target is a bodily tissue.

In some embodiments, said specified value is a square root of said signal.

In some embodiments, at least some of said signals are delayed signals.

In some embodiments, said convolution is a linear convolution in the lateral direction.

In some embodiments, said convolution is based, at least in part, on a Fourier transform.

In some embodiments, said calculating of said weighted sum comprises adjusting an intrinsic apodization function of said beamformed signal.

In some embodiments, said multiple transducers comprise a sparse array of transducers.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 12A-16D show experimental phantom results, according to several embodiments; and FIGS. 17A-17D, 18 show experimental in-vivo clinical results, according to several embodiments.

DETAILED DESCRIPTION

Figure 1:
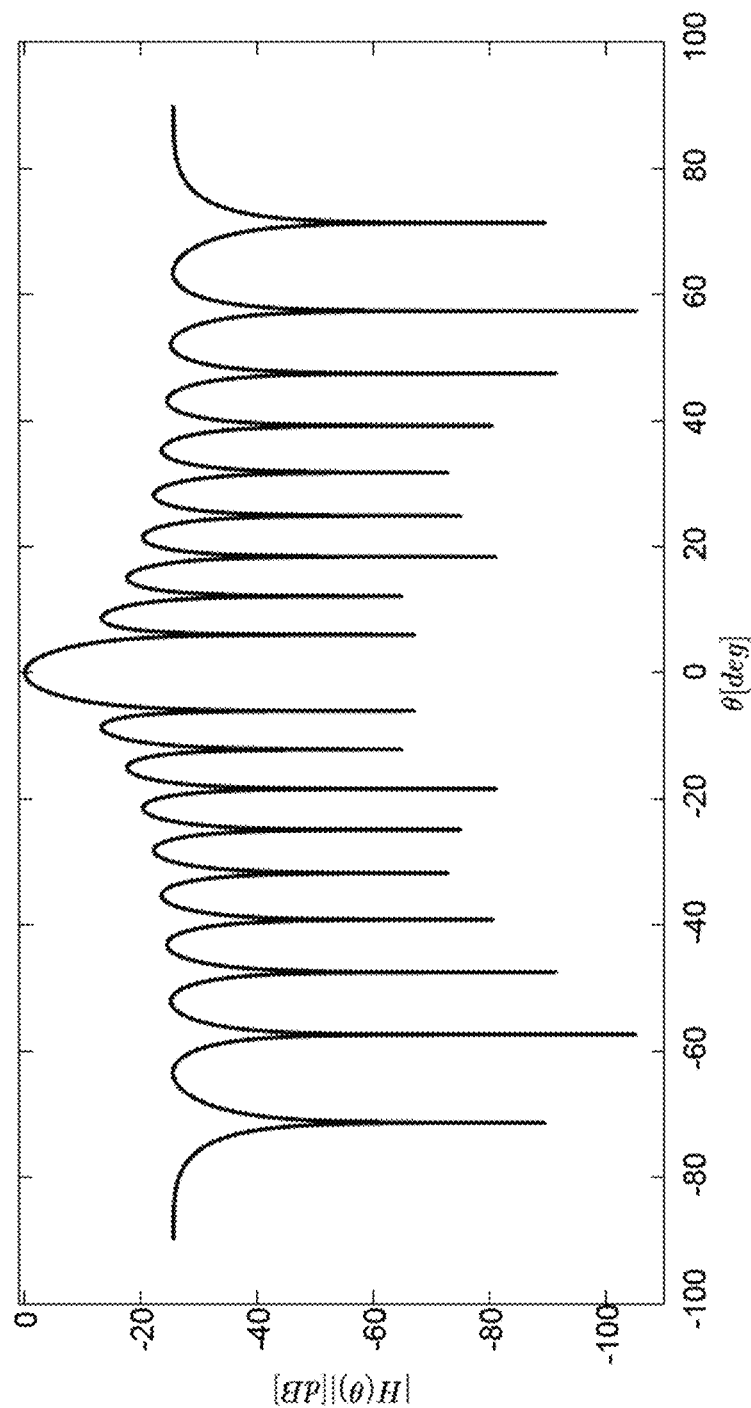
FIG. 1 shows a plot of a beam pattern generated by a standard DAS beamformer.

Disclosed herein are a system and method for nonlinear beamformer based on a convolutional beamforming algorithm (abbreviated COBA).

In some embodiments, the present algorithm achieves significant improvement of lateral resolution and contrast as compared to current beamforming methods. In addition, in some embodiments, the present algorithm can be implemented efficiently using a fast Fourier transform.

In some embodiments, the present disclosure also provides for two sparse beamformers with closed-form expressions for sensor locations, which result in similar beam patterns as other current methods, while using far fewer array elements. In some embodiments, the present disclosure provides for an array of elements comprising a minimal number of elements, which, in some embodiments, is on the order of the square root of the number used by, e.g., delay and sum (DAS) systems. In some embodiments, the present system outperforms DAS in terms of resolution and contrast, and the suggested beamformers offer a sizable element reduction while generating images with an equivalent or improved quality in comparison to DAS.

In a conventional ultrasound scanning process, short acoustic pulses are transmitted along a narrow beam from an array of transducer elements. During their propagation, echoes are scattered by acoustic impedance perturbations in the tissue, and detected by the array elements. The backscattered acoustic signals are then processed in a way referred to as beamforming to create a line in the image. The beamformer is designed to focus and steer the ultrasound transducer towards a desired direction or point in space. The main goal of the beamformer is to generate a beam pattern with a narrow main lobe and low side lobes. The beam main-lobe width dictates the system resolution, while the side-lobe level controls contrast so that the beam properties have a great impact on image quality.

As noted above, the standard beamforming technique is DAS, which consists of delaying and weighting the reflected echoes before summing them. While its simplicity and real-time capabilities make DAS widely used in ultrasound scanners, it exhibits limited imaging resolution and contrast. Increasing the number of elements, while keeping the array pitch below half a wavelength to avoid grating lobes, results in enhanced resolution. However, this increases channel data size and the system cost due to the receive electronics required for each element. Therefore, reducing the number of receiving channels while producing high quality images is of great importance.

Accordingly, in some embodiments, the present disclosure provides for a reduction in the number of receiving channels while preserving or improving the image quality in comparison to a DAS beamformer operating on the full array. In some embodiments, the present disclosure provides for a beamforming technique as well as two deterministic designs of sparse arrays based on it.

In some embodiments, a non-linear beamformer of the present disclosure is based on the convolution of the delayed signals prior to summation. The present beamformer can be implemented efficiently using the fast Fourier transform (FFT), thus making it suitable for real-time application. The beam pattern generated by the present beamformer shows its relation to the sum co-array, which has twice the size of the physical aperture and triangle-shaped apodization. Consequently, the present beamformer demonstrates significant improvement of lateral resolution and image contrast.

In some embodiments, the present disclosure further provides for a definition of sparse arrays based on the sum co-array, which combined with the present beamformer, leads to two designs of sparse convolutional beamformers that require fewer receiving elements than DAS. The first technique, based on a sparse convolutional beamforming algorithm (abbreviated SCOBA), utilizes significantly fewer elements while obtaining a beam pattern similar to that of DAS in terms of resolution. The second method, based on a sparse convolutional beamforming algorithm with super-resolution (abbreviated SCOBAR), offers increased resolution at the expense of a smaller, yet notable, channel reduction.

In some embodiments, the present disclosure further provides for the application of apodization directly on the sum co-array, in order to improve its contrast. Optimization of the sparse designs reveals that the minimal number of elements required to obtain the beam patterns achieved by the sparse convolutional beamformers (abbreviated SCOBA and SCOBAR) are both proportional to V, where N is the number of channels in the fully populated array. Thus, these approaches offer sizable element reduction without compromising image quality.

In some embodiments, the present disclosure further provides for simulations of point-reflectors and an anechoic cyst to provide qualitative and quantitative assessments of image quality using the proposed beamformers. Accordingly, the present algorithm is shown to achieve significant improvement of resolution and contrast compared to DAS. In addition, the present sparse convolutional beamformers (abbreviated SCOBA and SCOBAR) demonstrate similar and enhanced performance with respect to DAS while operating with a low number of channels.

In a uniform linear array (ULA) comprised of 2N−1 transducer elements aligned along the lateral axis x, the sensor locations $p_n$ are given by $$p_n = (nd, z=0) \quad n = -(N-1), \ldots, N-1, \quad (1)$$

where d is the spacing (pitch) between the centers of the individual elements and z denotes the axial axis. Upon reception, an energy pulse is backscattered from a point in space (r, θ), propagates through the tissue at speed c and is received by all array elements at a time depending on their locations. The signal received at the 0th element is denoted by $$f(t) = \tilde{f}(t) e^{jw_0 t}. \quad (2)$$

Here, $w_0$ is the transducer center frequency and $\tilde{f}(t)$ is the signal envelope. The sensors spatially sample the signal, such that the signal $f_n(t)$ at the nth element is given by $$f_n(t) = f(t - \tau_n) = \tilde{f}(t - \tau_n) e^{jw_0(t - \tau_n)}, \quad (3)$$

where $\tau_n$ is a time delay. To derive an expression for the delays, the following assumptions are introduced:

A1 (Narrow-Band) The signal f(t) is narrow-band, i.e., the bandwidth of the envelope is small enough so that $$\tilde{f}(t - \tau_n) \approx \tilde{f}(t), n = -(N-1), \ldots, N-1. \quad (4)$$

A2 (Far-Field) The point (r, θ) is in the far-field region of the array, thus, the input signal impinging on the array is considered to be a plane-wave.

Under the assumptions above, we can rewrite (3) as $$f_n(t)=\tilde{f}(t)e^{jw_0(t-\tau_n)}, \quad (5)$$

where $$\tau_n = \frac{d\sin\theta}{c}n,$$

i.e., the delays are approximated by phase shifts independent of r.

A beamformer processes each sensor output by a filter with impulse response $\tilde{g}_n(t)=g_n(t+\alpha_n)$ where $$\alpha_n = \frac{d\sin\theta_0}{c}n \quad (6)$$

for a direction of interest $$-\frac{\pi}{2} \leq \theta_0 \leq \frac{\pi}{2}.$$

Thus, the output of the nth element is $$y_n(t)=\tilde{g}_n(t) \overset{*}{t} f_n(t)=g_n(t+\alpha_n) \overset{*}{t} f_n(t-\tau_n) \quad (7)$$

where $\overset{*}{t}$ denotes temporal convolution. The beamformer then sums the output to obtain the array output $$y(t) = \sum_{n=-(N-1)}^{N-1} y_n(t). \quad (8)$$

In the frequency domain, (8) may be expressed as $$Y(\omega) = \sum_{n=-(N-1)}^{N-1} G_n(\omega)F(\omega)e^{-j\omega(\tau_n-\alpha_n)} \quad (9)$$
$$= F(\omega)\sum_{n=-(N-1)}^{N-1} G_n(\omega)e^{-j\omega(\tau_n-\alpha_n)},$$

where $Y(\omega)$, $F(\omega)$ and $G_n(\omega)$ are the temporal Fourier transforms of $y(t)$, $f(t)$ and $g_n(t)$ respectively.

To analyze the response of a beamformer to an input field, the input is assumed to be a unity amplitude plane wave $$f(t)=e^{jw_0 t}, \quad (10)$$

where $\tilde{f}(t) \equiv 1$. Substituting (10) into (9), we obtain $$Y(\omega) = \delta(\omega - \omega_0)\sum_{n=-(N-1)}^{N-1} G_n(\omega)e^{-j\omega(\tau_n-\alpha_n)} \quad (11)$$
$$= \delta(\omega - \omega_0)\sum_{n=-(N-1)}^{N-1} G_n(\omega_0)e^{-j\omega_0(\tau_n-\alpha_n)},$$

where $\delta(\omega)$ is the Dirac delta. Given the explicit expressions for $\tau_n$ and $\alpha_n$, (11) can be rewritten a function of $\theta$ $$Y(\omega, \theta) = \delta(\omega - \omega_0)\sum_{n=-(N-1)}^{N-1} G_n(\omega_0)e^{-j\omega_0 \frac{nd}{c}(\sin\theta-\sin\theta_0)}. \quad (12)$$

The sum on the right hand side of (12) is defined as the beam pattern of the beamformer $$H(\theta) \triangleq \sum_{n=-(N-1)}^{N-1} G_n(\omega_0)e^{-j\omega_0 \frac{nd}{c}(\sin\theta-\sin\theta_0)}. \quad (13)$$

For simplicity, it is assumed that $\theta_0=0$, which yields $$H(\theta) = \sum_{n=-(N-1)}^{N-1} G_n(\omega_0)e^{-j\omega_0 \frac{nd\sin\theta}{c}}. \quad (14)$$

The beam pattern represents the beamformer response to variations in the input field. In standard delay and sum (DAS) beamforming—

$$g_n(t)=w_n\delta(t), n=-(N-1),\ldots,N-1, \quad (15)$$

where $w_n$ is the weight of the nth element. Thus, $$H_{DAS}(\theta) = \sum_{n=-(N-1)}^{N-1} w_n e^{-j\omega_0 \frac{nd\sin\theta}{c}}. \quad (16)$$

FIG. 1 shows a plot of a beam pattern generated by a standard DAS beamformer. The main lobe width of the beam pattern affects system resolution, while the peak side lobe level determines image contrast and interference levels.

Denote the transducer wavelength by $\Delta=2\pi c/\omega_0$ and the array's aperture size by $L=2(N-1)d$. The angle $\theta_1$ of the first zero in the beam pattern is given by $$\sin\theta_1 = \frac{\lambda}{L}. \quad (17)$$

Hence, a large array or a high center frequency yields a narrow main lobe. In contrast, the magnitude of the side lobes is controlled by the weights $w_n$, known as the aperture function. The side lobes can be reduced by choosing an aperture function that is smooth like a Hanning window or a Gaussian shape. This, however, broadens the main lobe width, decreasing system resolution.

It should be noted that, in practice, ultrasound systems perform beamforming in the digital domain: analog signals are amplified and sampled by an analog to digital converter, preceded by an anti-aliasing filter. In addition, assumptions A1 and A2 above do not typically hold in ultrasound imaging. The signal f(t) is wide-band and imaging is performed in the near-field, leading to time delays that depend non-linearly on both r and $\theta$ as:

$$\tau_n = \frac{r + \sqrt{r^2 - 2ndr\sin\theta + (nd)^2}}{c}. \quad (18)$$

However, the approach taken here is convenient in introducing the major concepts, such as in lobe and side lobes which affect the image quality and is standard in the literature.

The present disclosure assumes an objective of designing arrays with fewer elements than 2N−1, together with a beamforming method which enables obtaining the beam pattern given by, e.g., A. Fenster and J. C. Lacefield, *Ultrasound Imaging and Therapy*, CRC Press, 2015, or otherwise an improved pattern in terms of resolution and image contrast. To that end, there is first introduced a new beamformer based on a lateral convolution operation and show that it leads to improved resolution by analyzing its beam pattern. Next, there are proposed two sparse beamforming techniques. The first beamformer uses fewer channels and demonstrates a lateral resolution similar to that of DAS, whereas the second beamformer achieves a twofold improvement in resolution at the expense of a smaller element reduction. Analysis of these approaches shows that the minimal number of elements required to obtain the desired beam patterns is proportional to $\sqrt{N}$.

In some embodiments, it is assumed that the element pitch d and the transducer center frequency $\omega_0$ are fixed. In addition, the array configurations are constrained so that all element locations satisfy $|x| \leq L/2$. Thus, it is shown that this limitation on the physical array aperture does not prevent creating an effective aperture which is larger in size than L. In some embodiments, an odd number of elements 2N−1 is assumed only for clarity of presentation, so that the center of the array is well-defined. However, the results presented herein hold also for an even number of elements.

There is disclosed herein a non-linear beamformer algorithm of the present invention. The disclosed beamformer is based on a convolution operation and can be implemented efficiently using the FFT. In some embodiments, a sum co-array is used to analyze the beam pattern of the present beamformer in comparison to DAS in terms of both resolution and image contrast.

In some embodiments, a beamformed signal may be defined as $$\bar{y}(t) = \sum_{n=-(N-1)}^{N-1} \sum_{m=-(N-1)}^{N-1} u_n(t) u_m(t), \quad (19)$$

where $$u_n(t) = \exp(j \angle y_n(t)) \sqrt{|y_n(t)|}, \quad -(N-1) \leq n \leq N-1, \quad (20)$$

with $\angle y_n(t)$ and $|y_n(t)|$ being the phase and modulus of $y_n(t)$ respectively.

In some embodiments, the beamformed signal may be inspired by, e.g. work transmit/receive pair array synthesis (see, e.g., Morten Fischer Rasmussen, Thomas Lehrmann Christiansen, Erik Vilain Thomsen, and Jorgen Arendt Jensen, "3-D imaging using row-column-addressed arrays with integrated apodization—Part I: Apodization design and line element beamforming", *IEEE Transactions on Ultrasonics, Ferroelectrics, and Frequency Control*, 62(5):947-958, 2015.)

The operation in (20) ensures that the amplitude of each product in (19) is on the same order of that of the signals $y_n(t)$ (see, e.g., the delayed signals $y_n(t)$ given by (7) as in DAS. This in turn means that the dynamic range of the resultant image will be similar to that obtained by DAS. For simplicity, unity weights $w_n = 1$ is assumed, wherein an extension for arbitrary apodization is given further below.

Computing (19) requires all possible signal pair combinations, $$\binom{2N-1}{2}$$

multiplications. Thus, conventionally the computation load for each pixel is $\mathcal{O}(N^2)$, which may lead to slow runtime. This complexity can be substantially reduced by noticing that the beamformed output (19) is equivalent to $$\bar{y}(t_i) = \sum_{n=-2(N-1)}^{2(N-1)} s_n(t), \quad (21)$$

where $$s_n = \sum_{(i,j:i+j=n)} u_i(t_i) u_j(t), \, n = -2(N-1), \ldots, 2(N-1). \quad (22)$$

Defining s(t) and u(t) as the length 2N−1 vectors whose entries are $s_n(t)$ and $u_n(t)$ receptively, then $$s(t) = u(t) \underset{s}{*} u(t), \quad (23)$$

where $\underset{s}{*}$ denotes a discrete linear convolution in the lateral direction. Thus, the vector s can be computed using an FFT by zero-padding u to length 2N−1, compute the Fourier transform of the result, square each entry and then perform the inverse Fourier transform to get s. Thus, the beamformed signal $\bar{y}(t)$ is obtained with low complexity of $\mathcal{O}(N \log N)$ operations.

The temporal products comprising the signal $\bar{y}(t)$ translate to a convolution in the frequency domain with respect to the axial direction, leading to direct current (DC) and harmonic components in the spectrum of $\bar{y}(t)$. Thus, an additional processing step is required to remove the baseband. The final output of the present convolutional beamformer is given by $$y_{COBA}(t) = h_{BP}(t) \underset{t}{*} \bar{y}(t) \quad (24)$$

where $h_{BP}(t)$ is a band-pass (BP) filter centered at the harmonic frequency $2\omega_0$.

In some embodiments, an exemplary algorithm 1 of the present beamformer may be given as follows:
Input: Delayed signals $y_n(t)$, weights $w_n$.
1: Compute $u_n(t) = \exp j \angle y_n(t) \sqrt{|y_n(t)|}$.
2: Set weights $$\tilde{w}_n = \frac{w_n}{(2N-1) - |n|}.$$

3: Calculate $$s(t) = u(t) \underset{s}{*} u(t)$$

using FFT.
4: Evaluate the weighted sum $$\bar{y}(t) = \sum_{n=-2(N-1)}^{2(N-1)} \tilde{w}_n s_n(t).$$

5: Apply a band-pass filter $$y_{COBA}(t) = h_{BP}(t) \underset{t}{*} \bar{y}(t).$$

Output: Beamformed signal $y_{COBA}(t)$.
In some embodiments, the weight-setting stage (stage 2 in algorithm 1) is optional.

In some embodiments, the present beamformer involves computing pair-wise products of the signals as in filtered delay multiply and sum (FDMAS). However, in contrast to FDMAS, it consists of all possible products, including the self-products for n=m and repetitions created by interchanging n and m. This allows avoiding the high computational complexity and partial energy loss which FDMAS suffers from. In addition, the FDMAS does not consider element reduction.

In some embodiments, as noted above, the beam pattern of the present convolutional beamformer outperforms standard DAS beamforming in terms of lateral resolution and image contrast. For example, when using the following definitions:

Definition 1 Position Set: Consider a linear array with d being the minimum spacing of the underlying grid on which sensors are assumed to be located. The position set is defined as an integer set I where n∈I if there is a sensor located at nd.

In some embodiments, a linear array with position set I is referred to as a linear array I.

Definition 2 Sum Co-Array: Consider a linear array I. Define the set $$\tilde{S}_I = n+m : n, m \in I. \tag{25}$$

$\tilde{S}_I$ includes repetitions of its elements, wherein set $S_I$ is referred to as the sumset of I, which consists of the distinct elements of $\tilde{S}_I$. The sum co-array of f is defined as the array whose position set is $S_I$.

As an example, the sum co-array of an M element ULA is another ULA with 2M−1 elements. The number of elements in the sum co-array directly determines the number of non-zeros in the convolutional signal (e.g., as given by Jorgen Arendt Jensen and Niels Bruun Svendsen, "Calculation of pressure fields from arbitrarily shaped, apodized, and excited ultrasound transducers", *IEEE Transactions on Ultrasonics, Ferroelectrics, and Frequency Control*, 39(2): 262-267, 1992).

Definition 3 Intrinsic Apodization: Consider a linear array I and define a binary vector 1 whose nth entry is 1 if n∈I and zero otherwise. The intrinsic apodization is an integer vector defined as $$a = 1_I * 1_I. \tag{26}$$

The intrinsic apodization vector is related to $S_I$ and $\tilde{S}_I$ in the following way. For every n∈$S_I$ the entry $a_n$ denotes the number of occurrences of n in $\tilde{S}_I$.

To derive an expression for the beam pattern of the convolutional beamformer the input signal is assumed to be $f(t) = e^{j\omega_0 t}$, impinging on the array at direction θ. Consequently, there is obtained $$u_n(t) = e^{j\omega_0 t} e^{-j\omega_0 \tau_n}, \tag{27}$$

where $\tau_n$ is given by (5). Substituting (27) into (19) we have $$\tilde{y}(t) = \sum_{n=-(N-1)}^{N-1} \sum_{m=-(N-1)}^{N-1} e^{j2\omega_0 t} e^{-j\omega_0(\tau_n + \tau_m)} \tag{28}$$

$$= e^{j2\omega_0 t} \sum_{n,m=-(N-1)}^{N-1} e^{-j\omega_0(\tau_n + \tau_m)}.$$

Following band-pass filtering, there is provided $$y_{COBA}(t) = \left(h_{BP}(t) * e^{j2\omega_0 t}\right) \sum_{n,m=-(N-1)}^{N-1} e^{-j\omega_0(\tau_n + \tau_m)}. \tag{29}$$

in the Fourier domain $$Y_{COBA}(\omega) = \delta(\omega - 2\omega_0) H_{BP}(2\omega_0) \sum_{n,m=-(N-1)}^{(N-1)} e^{-j\omega_0(\tau_n + \tau_m)}, \tag{30}$$

where $H_{BP}(\omega)$ is the Fourier transform of the band-pass filter $h_{BP}(t)$. Assuming that $H_{BP}(2\omega_0) = 1$, the beam pattern generated by the present beamformer algorithm is $$H_{COBA}(\theta) = \sum_{n,m=-(N-1)}^{N-1} e^{-j\omega_0(\tau_n + \tau_m)} = \sum_{n,m=-(N-1)}^{N-1} e^{-j\omega_0 \frac{d\sin\theta}{c}(n+m)}, \tag{31}$$

where the last equation is obtained by substituting the explicit expression for $\tau_n$.

The sum in (31) is the product of two polynomials $H_{COBA}(\theta) = H_{DAS}(\theta) H_{DAS}(\theta)$ with $H_{DAS}(\theta)$ given by (16) assuming $w_n = 1$. In some embodiments, $H_{COBA}(\theta)$ can be written as a single polynomial $$H_{COBA}(\theta) = \sum_{n=-2(N-1)}^{2(N-1)} a_n e^{-j\omega_0 \frac{d\sin\theta}{c} n}, \tag{32}$$

where $a_n$ are triangle-shaped intrinsic apodization weights given by (26).

Figure 2:
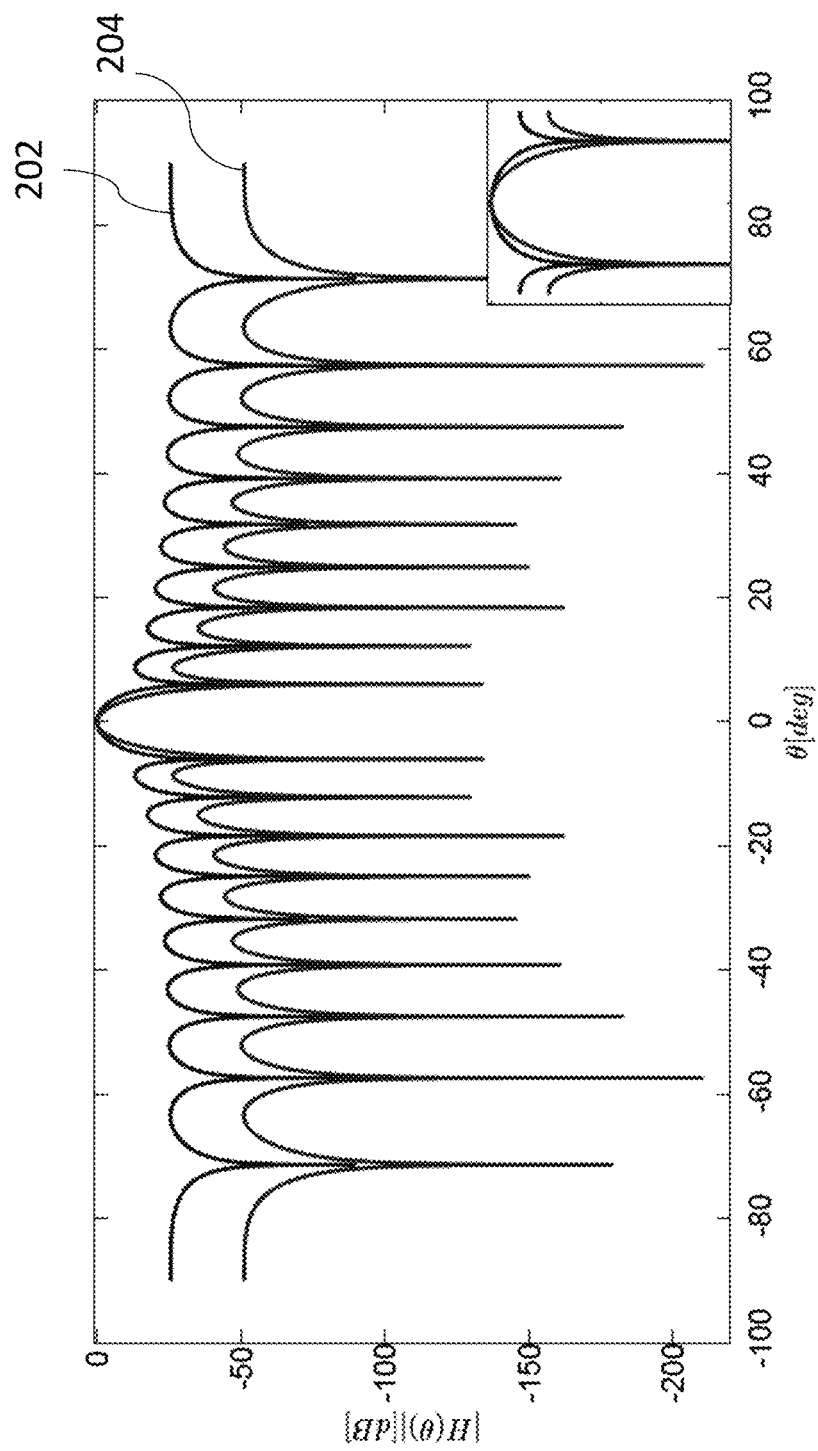
FIG. 2 shows beam pattern magnitudes of DAS and a beam formed in accordance with the algorithm disclosed herein, according to an embodiment.

Equation (32) can be thought of as the beam pattern of a DAS beamformer operating on the sum co-array. This virtual array is twice the size of the physical one, leading to a resolution that is twice as good as the standard resolution. In addition, the apodization of the sum co-array reduces the side lobes, thus, the convolutional beamformer results in improved image contrast, as demonstrated in FIG. 2, showing beam pattern magnitude of DAS (graph 202) and the present algorithm (204) for $$N = 10, w_n = 1, \lambda = 1, d = \frac{1}{2},$$

as well as a zoomed-in view of the main lobe.

As noted above, the present convolutional beamformer algorithm leads to better resolution and contrast with respect to DAS. An analysis of its beam pattern showed that its performance depends on the sum co-array, rather than the physical array.

Given a uniform linear array (ULA) of 2N−1 elements with position set I=−(N−1), . . . , (N−1), the present disclosure aims to remove some of its elements to create a thinned array, without degrading image quality. To this end, the following is defined:

Definition 4 Sparse Array: Consider a ULA with position set I. A sparse array with respect to I is a thinned array, created by removing part of the elements, which satisfies $$J \subset I \subseteq S_J, \tag{33}$$

where J and $S_J$ are integer sets indicating the elements positions of the thinned array and of its sum co-array respectively.

A sparse array J according to the definition above must be a strict sub-array of I, i.e., the number of elements in J is strictly smaller than that of I. In addition, performing convolutional beamforming using J is equivalent to applying DAS beamforming on the sum co-array $S_J$ which by Definition 4 has an aperture at least as large as the original ULA I. Thus, it results in a beam pattern which is equal or better in resolution than the beam pattern generated by a DAS beamformer applied to I.

Accordingly, the present disclosure provides for a simple closed form sparse array design which leads to a large element reduction. Assume N is not a prime number, so that it can be factored as N=AB where A, B∈ $\mathbb{N}^+$. Given such a decomposition, the following array may be defined:

$$U_A = -(A-1), \ldots, 0, \ldots, A-1,$$

$$U_B = nA:n = -(B-1), \ldots, 0, \ldots, B-1. \quad (34)$$

In some embodiments, other and/or different array designs may be used, wherein in each case, the sum co-array is full, i.e., it is contiguous.

Figure 3:
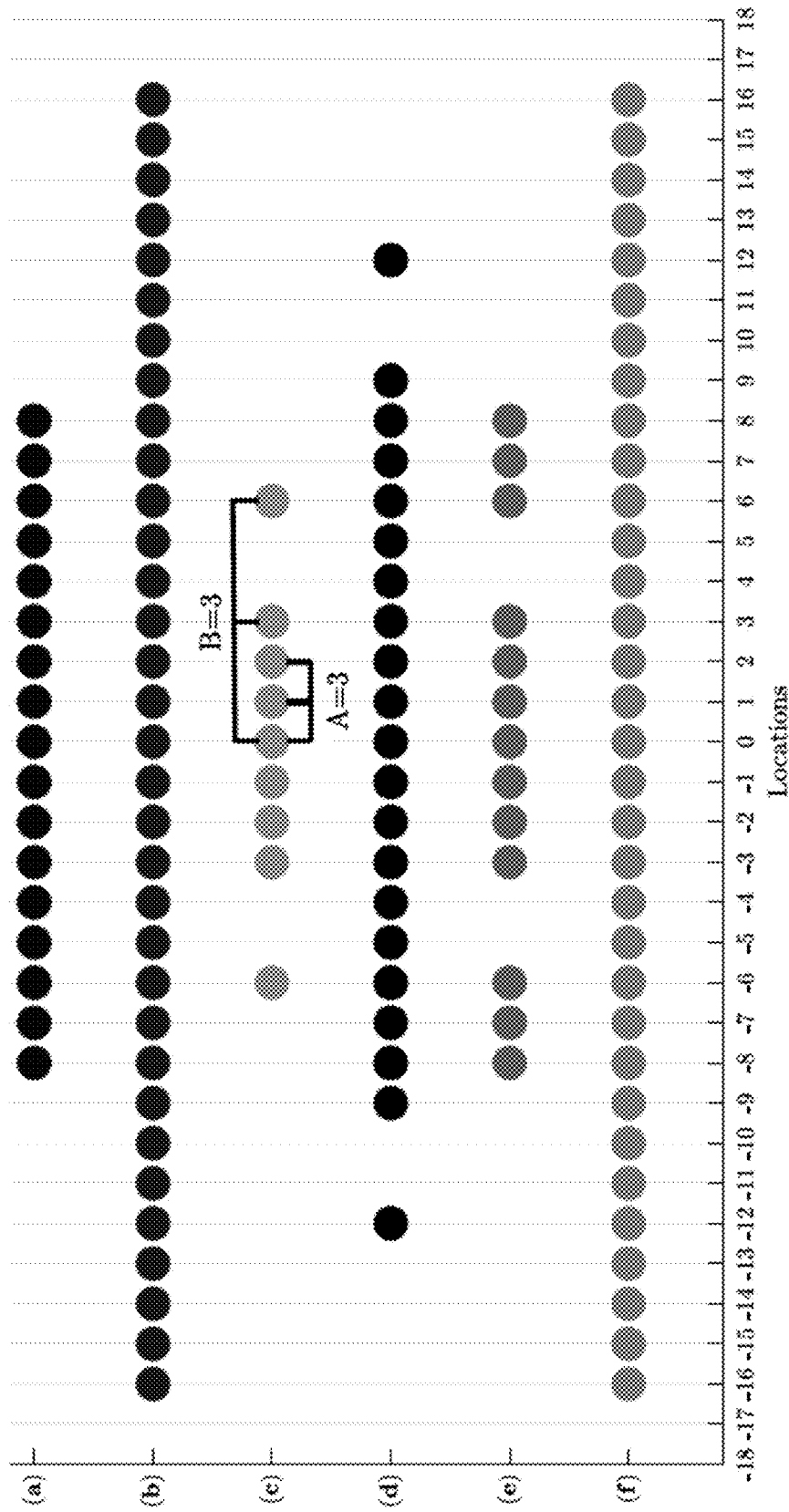
FIG. 3 illustrates various ultrasound element arrays, according to an embodiment.

An illustration of this array for N=9, A=3 and B=3 is seen in FIG. 3. Element positions of (a) ULA I=[−8,8], (b) sum co-array $S_I$=[−16,16], (c) sparse array U given by (36), (d) sum co-array $S_U$, (e) sparse array V defined by (45), and (f) sum co-array $S_V$. In FIG. 3, the element spacing is d=1, N=9 and A=3, B=3

Let $U_A + U_B = n+m: n \in U_A, m \in U_B$. Then $$U_A + U_B = -(AB-1), \ldots, 0, \ldots AB-1)$$

$$= -(N-1), \ldots, 0, \ldots, N-1$$

$$= I. \quad (35)$$

Thus, denoting by U ⊂ I the array geometry defined as $$U = U_A \cup U_B, \quad (36)$$

it holds that $$I \subseteq S_V \quad (37)$$

where $S_U$ is the sum-set of U.

Thus, the family of sets (36) satisfy (33) where the number of elements in each set is 2A+2B−3. As an example, for N=9 and A=3, B=3 the set U has only 9 elements out of 17 in the full array, as shown in FIG. 3.

Based on U, a sparse convolutional beamforming algorithm (abbreviated SCOBA) is disclosed, which computes the following signal $$\bar{y}_{SCOBA}(t) = \Sigma_{n \in U} \Sigma_{m \in U} u_n(t) u_m(t), \quad (38)$$

where $u_n(t)$ is defined in (20). Namely, the COBA algorithm of the present disclosure is performed only on the outputs of the elements in U. As before, (38) can be written using the sum co-array $S_U$ $$\bar{y}_{SCOBA}(t) = \Sigma_{n \in S_U} s_n(t), \quad (39)$$

where $$s_n(t) = \Sigma_{(i,j) \in U: i+j=n} u_i(t) u_j(t) \quad (40)$$

Thus, the final output of SCOBA is given by $$y_{SCOBA}(t) = h_{BP}(t) * \bar{y}_{SCOBA}(t). \quad (41)$$

Computing (39) can be performed using appropriate zero-padding and FFT in $\mathcal{O}(N \log N)$ operations or directly by pair-wise products with complexity $\mathcal{O}((A+B)^2)$ which may be lower. The proposed beamformer is summarized in exemplary algorithm 2:

Input: Delayed signals $y_n$, weights $w_n$, parameters A, B.
1: Construct the set U using (36) and its sumset $S_U$.
2: Compute $u_n(t) = \exp j \angle y_n(t) \sqrt{|y_n(t)|}$, n∈ U.
3: Calculate $a = 1_U * 1_U$.
4: Set weights $$\tilde{w}_n = \frac{w_n}{a_n}, n \in S_U.$$

5: For all n∈ $S_U$ compute $s_n(t)$ using (40).
6: Evaluate the weighted sum $$\bar{y}(t) = \Sigma_{n \in S_U} \tilde{w}_n s_n(t).$$

7: Apply a band-pass filter $$y_{SCOBA}(t) = h_{BP}(t) * \bar{y}(t).$$

Output: Beamformed signal $y_{SCOBA}(t)$.

The beam pattern produced by SCOBA may be analyzed following similar steps to those presented above, to lead to $$H_{SCOBA}(\theta) = \Sigma_{n,m \in U} e^{-j\omega_0 \frac{d \sin \theta}{c}(n+m)} = \Sigma_{n \in S_U} u_n e^{-j\omega_0 \frac{d \sin \theta}{c} n}, \quad (42)$$

where $1_U * 1_U$ is the intrinsic apodization of SCOBA. In some embodiments, (42) can be rewritten as $$H_{SCOBA}(\theta) = \Sigma_{n \in I} u_n e^{-j\omega_0 \frac{d \sin \theta}{c} n} + \Sigma_{m \in S_U/I} u_m e^{-j\omega_0 \frac{d \sin \theta}{c} m}, \quad (43)$$

where $S_U/I = m \in S_U : m \notin I$.

Figure 4:
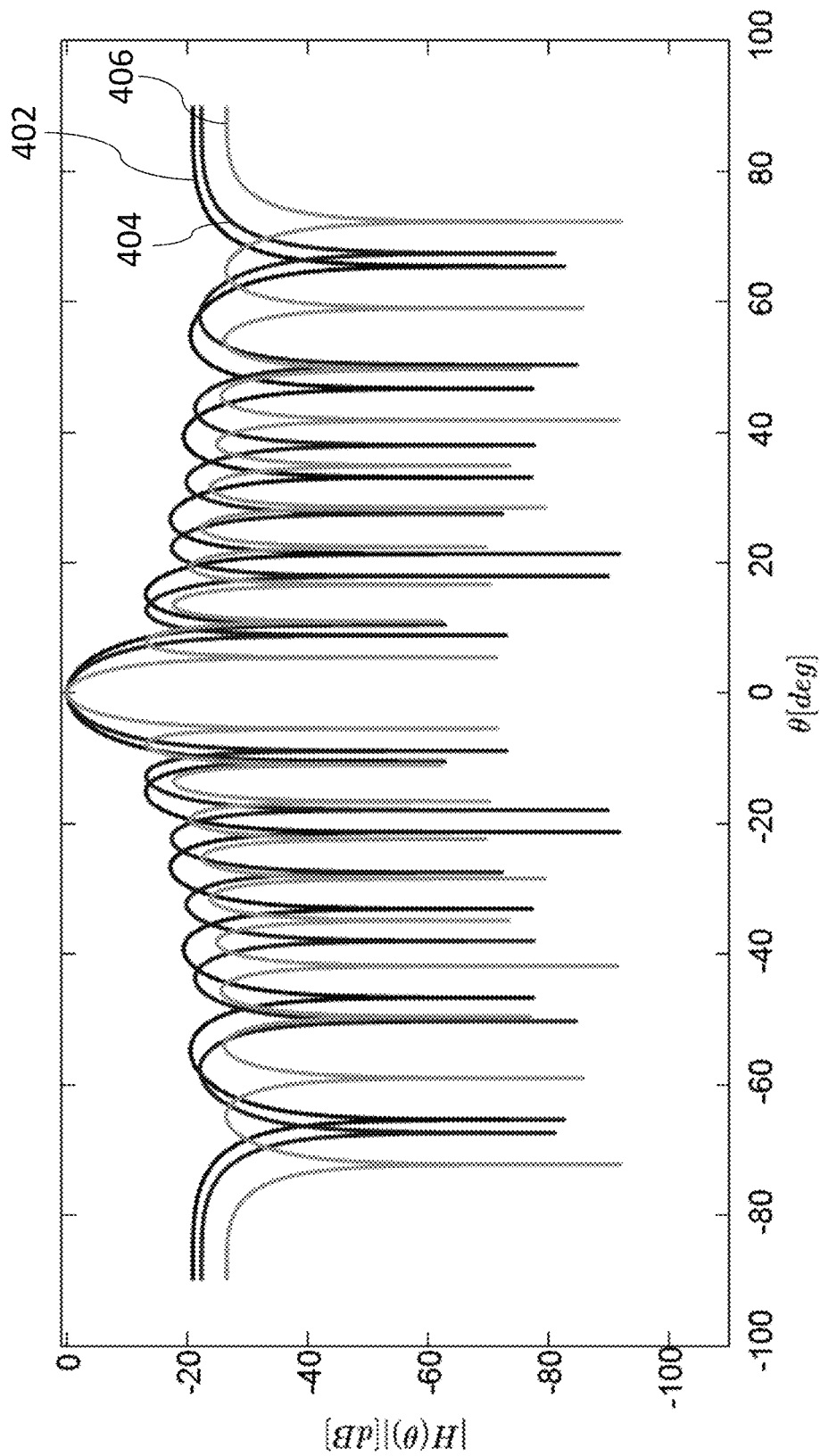
FIG. 4 illustrates the beam patterns of DAS and various beam patterns, according to several embodiments.

The first sum in the equation above ensures the resolution of SCOBA is at least as good as the resolution of a DAS beamformer applied on the full array I. The second sum, on the right hand side of (43), provides additional degrees of freedom that may be used to improve the resolution. The image contrast depends on the apodization $u_n$ which can be adjusted as shall be further described below. FIG. 4 illustrates the beam patterns of DAS (graph 402), SCOBA (graph 404), and SCOBAR (graph 406), for $$N = 6 \text{ and } A = 3, B = 2, \lambda = 1, d = \frac{1}{2}.$$

The number of elements required for SCOBA is 2A+2B−3, thus, it leads to a family of beamformers in which each beamformer demonstrates a different level of element reduction, controlled by the parameters A, B. While a large number of elements may be favorable in the presence of noise, it also increases the mutual coupling, which is the electromagnetic interaction between adjacent sensors that has an adverse effect on obtaining a desired beam pattern.

As noted above, the disclosed COBA algorithm achieves twice the standard resolution. Following that, a sparse array design is further disclosed, to create a beamformer which uses fewer elements and yields a resolution that is comparable to the standard one. In some embodiments, a family of sparse beamformers is disclosed, with enhanced resolution that is equivalent to that of the COBA algorithm, thereby combining the best of both worlds. In some embodiments, this technique may be referred to as sparse convolutional beamforming algorithm with super-resolution (abbreviated SCOBAR).

In some embodiments, the array configuration used in SCOBA may be extended by constructing an additional array as $$U_C = n : |n| = N-A, \ldots, N-1. \quad (44)$$

Then, a sparse array geometry may be given by $$V = U_A \cup U_B \cup U_C. \quad (45)$$

As shown in FIG. 3, V may be obtained by adding to U two small ULAs of size A−1 at its edges. It can then be verified that $$V \subset I \subset S_V = S_I, \quad (46)$$

i.e., the sum co-array of V is equal to the sum co-array of the full array I. SCOBAR uses the array sensors given by V to compute the signal $$\bar{y}_{SCOBAR}(t) = \Sigma_{n \in V} \Sigma_{m \in V} u_n(t) u_m(t)$$

$$= \Sigma_{n \in S_V} n s_n(t) \quad (47)$$

where $u_n(t)$ is defined in (20) and $$s_n(t) = \Sigma_{(i,j) \in V: i+j=n} u_i(t) u_j(t). \quad (48)$$

The final output of SCOBAR is given by $$y_{SCOBAR}(t) = h_{BP}(t) * \bar{y}_{SCOBAR}(t). \quad (49)$$

Similar to SCOBA, (47) can be calculated using FFT in $\mathcal{O}(N \log N)$ operations or directly in $\mathcal{O}((A+B)^2)$. A summary of SOCBAR is provided in exemplary Algorithm 3:

Input: Delayed signals $y_n$, weights $w_n$, parameters A, B.
1: Construct the set V using (45) and its sumset $S_V$.
2: Compute $u_n(t) = \exp j \angle y_n(t) \sqrt{|y_n(t)|}$, $n \in V$.
3: Calculate $a = 1_V * 1_V$.
4: Set weights $$\tilde{w}_n = \frac{w_n}{a_n}, n \in S_V.$$

5: For all $n \in S_V$ compute $s_n(t)$ using (48).
6: Evaluate the weighted sum $$\bar{y}_{SCOBAR}(t) = \Sigma_{n \in S_V} \tilde{w}_n s_n(t).$$

7: Apply band-pass filter $$y_{SCOBAR}(t) = h_{BP}(t) *_t \bar{y}_{SCOBAR}(t).$$

Output: Beamformed signal $y_{SCOBAR}(t)$.

Following similar arguments as for COBA and SCOBA, the beam pattern of SCOBAR is $$H_{SCOBAR}(\theta) = \sum_{n,m \in V} e^{-j\omega_0 \frac{d \sin\theta}{c}(n+m)} = \quad (50)$$

$$\sum_{n \in S_V} v_n e^{-j\omega_0 \frac{d \sin\theta}{c} n} = \sum_{n=-2(N-1)}^{2(N-1)} v_n e^{-j\omega_0 \frac{d \sin\theta}{c} n}$$

where $v = 1_V * 1_V$ and the last equality is due to the fact that $S_V = S_I = -2(N-1), \ldots, 2(N-1)$. The latter implies that the lateral resolution of SCOBAR is similar to that of COBA, twofold better than the standard one, as shown in FIG. 3.

The weights $v_n$ can be modified to control the image contrast as described further below.

The number of elements required by SCOBAR is 4A+2B−5, thus, the improved resolution is at the expense of a smaller element reduction in comparison with SCOBA.

As noted above, the image contrast is governed by the peak side lobe level. Amplitude apodization (see, e.g., Fenster [2015]) is an important tool used for suppressing side lobes, leading to improved contrast. Typical apodization functions include Hanning, Hamming, or Gaussian amplitude weighting of the elements which lowers the side lobes at the expense of widening the main lobe width, i.e., worsening the lateral resolution. Therefore, there is a tradeoff between lateral resolution and contrast and a judicious choice of the apodization must be made based on the clinical application.

Figure 5A:
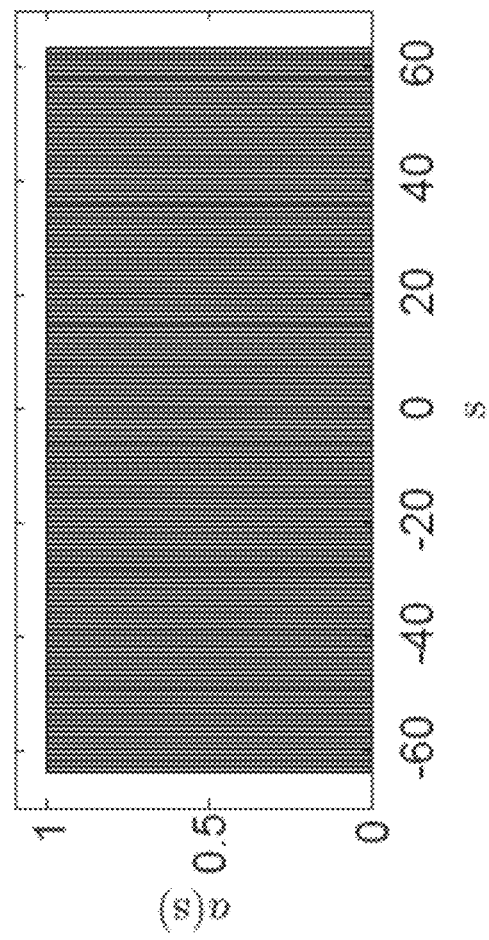
FIGS. 5A-5D show the intrinsic apodization of DAS and various beamformers, according to several embodiments.
Figure 5B:
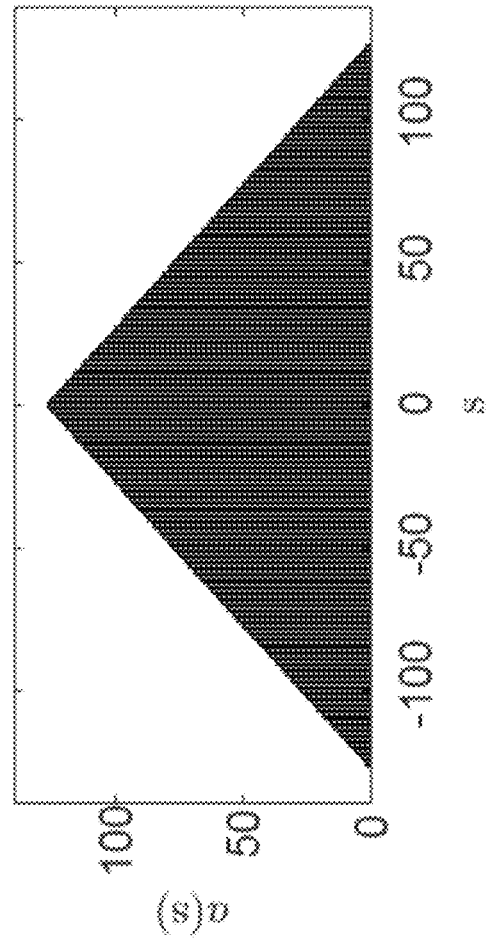
Figure 5C:
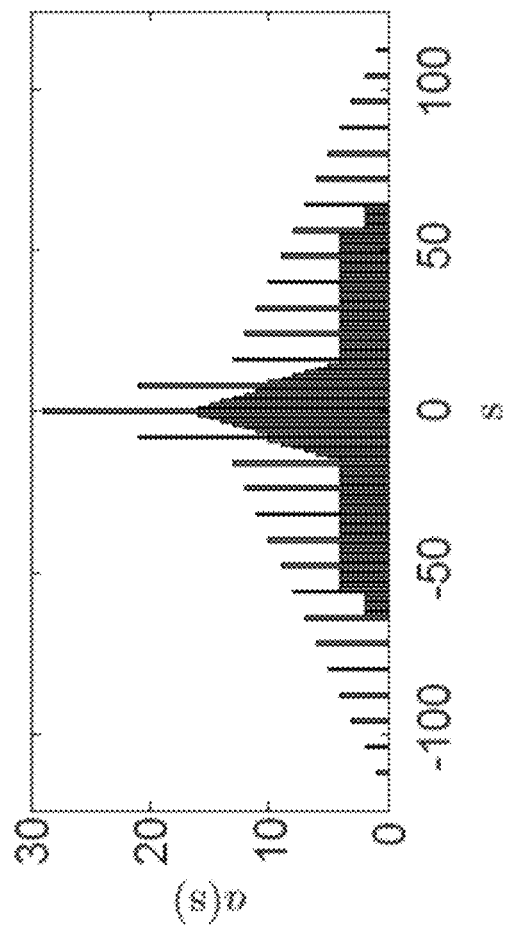
Figure 5D:
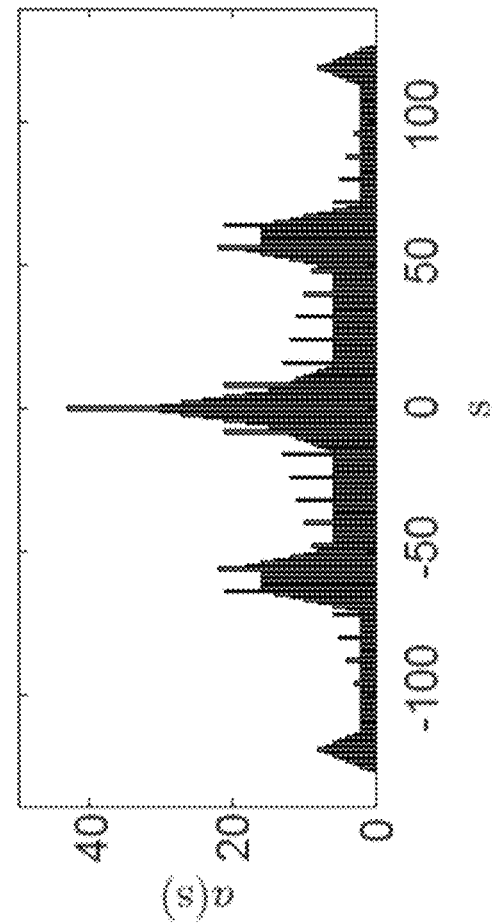

As noted above, the concept of intrinsic apodization arises in the presently disclosed beamformers. This concept is extended to a standard DAS beamformer by assuming the array has intrinsic weights of unity. FIGS. 5A-5D show the intrinsic apodization of the different beamformers. FIG. 5A shows DAS with 127 elements, FIG. 5B shows COBA with 127 elements, FIG. 5C shows SCOBA with A=B=8, and FIG. 5D shows SCOBAR with A=B=8.

For a DAS (FIG. 5A) beamformer, the intrinsic apodization function is constant over the elements and equal to 1, whereas, for COBA (FIG. 5B) the apodization shows a triangle-shaped apodization which suppresses side lobes. The intrinsic apodization functions of SCOBA and SCOBAR depend on the parameters A and B, and should be analyzed to avoid unwanted side lobes.

To address this issue, in some embodiments, a simple adjustment to the apodization function is disclosed, which takes into account the intrinsic apodization. Given a desired apodization function with weights $w_n$, a modified apodization function is defined $$\tilde{w}_n = \frac{w_n}{a_n}, \quad (51)$$

where $a_n$ are the intrinsic weights assumed to be non-zero. Then, these weights are applied on the sum co-array by computing the weighted sum $$\bar{y}(t) = \Sigma_n \tilde{w}_n s_n(t), \quad (52)$$

prior to band-pass filtering. This ensures that the resulting beam pattern will have weights equal to $w_n$ as desired.

The intrinsic apodization functions of COBA and SCOBAR both have only non-zeros, thus, any apodization can be achieved using (51). In the case of SCOBA, the intrinsic apodization has zeros, leading to discontinuities in the beam pattern which may be considered as a drawback at first glance. However, this is expected since the intrinsic apodization of SCOBA is designed to have non-zeros in the range −[N−1, N−1], similar to DAS beamformer. Thus, any apodization function obtained by DAS can be attained by SCOBA. In fact, the intrinsic apodization of SCOBA has more degrees of freedom (non-zeros) than DAS as shown in (43), allowing the use of an extended family of apodization functions.

As noted before, the number of elements used by SCOBA and SCOBAR is controlled by the parameters A and B. In some embodiments, expressions for A and B may be derived, leading to a minimal number of sensors required by the proposed beamformers.

In some embodiments, for SCOBA, minimizing the number of elements can be cast as the following optimization problem:

$$A^*, B^* = \underset{A,B \in \mathbb{N}}{\operatorname{argmin}} \, 2(A+B) - 3 \quad (53)$$

subject to $AB = N$.

When N is a prime number, there are only two feasible solutions which are optimal given by A=N, B=1 and vice versa; both result in a fully populated array. Hence, a case may be considered where N is not prime and (53) becomes a combinatorial optimization problem. A closed form solution is presented in the following theorem:

Theorem 1 Given an arbitrary $N \in \mathbb{N}^+$, define the sets $$D_1 = \{m \in \mathbb{N} : m \mid N, \ m \leq \sqrt{N}\}, \quad (54)$$

$$D_2 = \{m \in \mathbb{N} : m \mid N, \ m \geq \sqrt{N}\},$$

where m|N indicates that m is a divisor of N. The optimal solutions for (53) are $$A^* = \max(D_1) \text{ and } B^* = \min(D_2),$$

$$A^* = \min(D_2) \text{ and } B^* = \max(D_1). \quad (55)$$

When N is a perfect square, we have a single optimal solution $$A^* = B^* = \sqrt{N}. \quad (56)$$

Proof.

$$A^*, B^* = \underset{A,B \in \mathbb{N}}{\operatorname{argmin}} \ A + B \quad (57)$$

$$\text{subject to } AB = N.$$

The inequality of the arithmetic and geometric means that $$\sqrt{AB} \leq \frac{A+B}{2}. \quad (58)$$

Thus, the objective function is lower bounded by $2\sqrt{N}$. Equality is obtained in (58) if and only if $A=B=\sqrt{N}$. Thus, this choice attains the lower bound and is optimal, which concludes the proof.

Theorem 1 implies that the minimal number of elements required by SCOBA is proportional to $\sqrt{N}$ and the beamformed signal given by (49) can be computed with a low complexity of $\mathcal{O}(N)$.

As for SCOBAR, note that when B=1, $U_C=U_A$ and A=N, leading to the trivial case where the array is full, hence, we assume that B>1. In this case, the minimal number of elements required by SCOBAR is given by the solution to $$A^*, B^* = \arg \underset{A,B \in \mathbb{N}, B>1}{\min} \ 2(2A+B) - 5 \quad (59)$$

$$\text{subject to } AB = N.$$

When N is prime, the only feasible and hence optimal solution is A=1 and B=N which is trivial. Therefore, we address below the case where N is not prime. A closed form solution is obtained in the next theorem.

Theorem 2 Given an arbitrary $N \in \mathbb{N}^+$, define the sets $$D_3 = \{m \in \mathbb{N} : m \mid 2N, \ m \leq \sqrt{2N}\}, \quad (60)$$

$$D_4 = \{m \in \mathbb{N} : m \mid 2N, \ m \geq \sqrt{2N}\}.$$

Denote by $\mathbb{E}$ the set of even integers. The optimal solutions for (59) are given by the following cases: [label=( )]

1. $\max(D_3) \in \mathbb{E}$, $\min(D_4) \in \mathbb{E}$ $$A^* = \max(D_3)/2 \text{ and } B^* = \min(D_4),$$

$$A^* = \min(D_4)/2 \text{ and } B^* = \max(D_3). \quad (61)$$

2. $\max(D_3) \notin \mathbb{E}$, $\min(D_4) \notin \mathbb{E}$ $$A^* = \max(D_3)/2 \text{ and } B^* = \min(D_4). \quad (62)$$

3. $\max(D_3) \notin \mathbb{E}$, $\min(D_4) \in \mathbb{E}$ $$A^* = \min(D_4)/2 \text{ and } B^* = \max(D_3). \quad (63)$$

When 2N is a perfect square, there is a single solution $$A^* = \frac{\sqrt{2N}}{2}, \ B^* = \sqrt{2N}. \quad (64)$$

Proof. For the special case when 2N is a perfect square, (59) is equivalent to $$A^*, B^* = \underset{A,B \in \mathbb{N}, B>1}{\operatorname{argmin}} \ 2A + B \quad (65)$$

$$\text{subject to } AB = N.$$

Once more, using the inequality of arithmetic and geometric means, $$\sqrt{2AB} \leq \frac{2A+B}{2}. \quad (66)$$

Consequently, the objective value is lower bounded by $2\sqrt{2N}$. This bound is attained by choosing $$A = \sqrt{\frac{N}{2}} \text{ and } B = \sqrt{2N}.$$

Theorem 2 indicates that SCOBAR requires a minimal number of sensors which is on the order of $\sqrt{2N}$. The beamformed signal can be obtained in complexity $\mathcal{O}(N)$, similar to SCOBA. Note, however, that while SCOBAR demonstrates almost twofold improvement in resolution, the increase in the number of elements, compared to SCOBA, is roughly only by a factor of $\sqrt{2}$.

With the purpose of reducing cost and size, one may desire to design a compact probe with a small physical aperture. While the size of the physical aperture using COBA and SCOBAR is fixed and given by L=(2N−1)d, for SCOBA it is equal to $\tilde{L}$=2A(B−1)d where B>1, and thus can be minimized using an appropriate choice of A and B. This objective can be formulated as follows $$A^*, B^* = \underset{A,B \in \mathbb{N}, B>1}{\operatorname{argmin}} \ A(B-1) \quad (67)$$

$$\text{subject to } AB = N.$$

The solution to (67) is given by the next theorem.

Theorem 3 Consider a non-prime number $N \in \mathbb{N}^+$. Denote by D the set of the non-trivial divisors of N, defined as $$D = \{m \in \mathbb{N} : m \mid N, 1 < m < N\}. \quad (68)$$

Then, the optimal solution to (67) is $$A^* = \max(D), B^* = \min(D). \tag{69}$$

Proof. Using the fact that $A(B-1)=N-A$, we rewrite (67) as $$A^*, B^* = \underset{A,B \in \mathbb{N}, B>1}{\operatorname{argmin}} A \tag{70}$$

subject to $AB = N$.

As can be seen from (70), the optimal $A$ is the maximal non-trivial divisor of $N$, i.e., $A^* = \max(D)$. Consequently, $$B^* = \frac{N}{A^*} = \min(D)$$

which concludes the proof.

Theorem 3 implies that when $N=2M$ with $M \in \mathbb{N}^+$ the optimal choice is $A=M$ and $B=2$, which leads to a ULA with a physical aperture that is twice of that of the original ULA. In other words, performing SCOBA on a given ULA is equivalent to performing COBA on a ULA with half the size. Note, however, that the number of elements in this case is $2M+1=N+1$, which is much larger than the minimal number achieved by Theorem 1.

Experimental Results

In this section, the performance of the disclosed beamformers is evaluated in comparison to DAS. The resolution and contrast are first evaluated using Field II simulator in MATLAB. Following that, the methods are applied on phantom data, scanned using a Verasonics imaging system, and on in vivo cardiac data acquired from a healthy volunteer.

In the following experiments, apodization is not applied upon reception for DAS and COBA. For relevant comparison, weights in SCOBA are employed to create an effective apodization of ones as in DAS. For SCOBAR, weights are applied to yield an effective triangle-shaped apodization as in COBA. The full transducer array is used for transmission and element reduction is performed only on the receive end.

In both simulations presented here, an array consisting of 127 elements was used, with an element width of 440 μm, a height of 6 mm, and a kerf of 0.0025 mm. During transmission, the transducer generated a Hanning-windowed 2-cycle sinusoidal pulse with a center frequency of 3.5 MHz and a focal depth of 50 mm.

Figure 6:
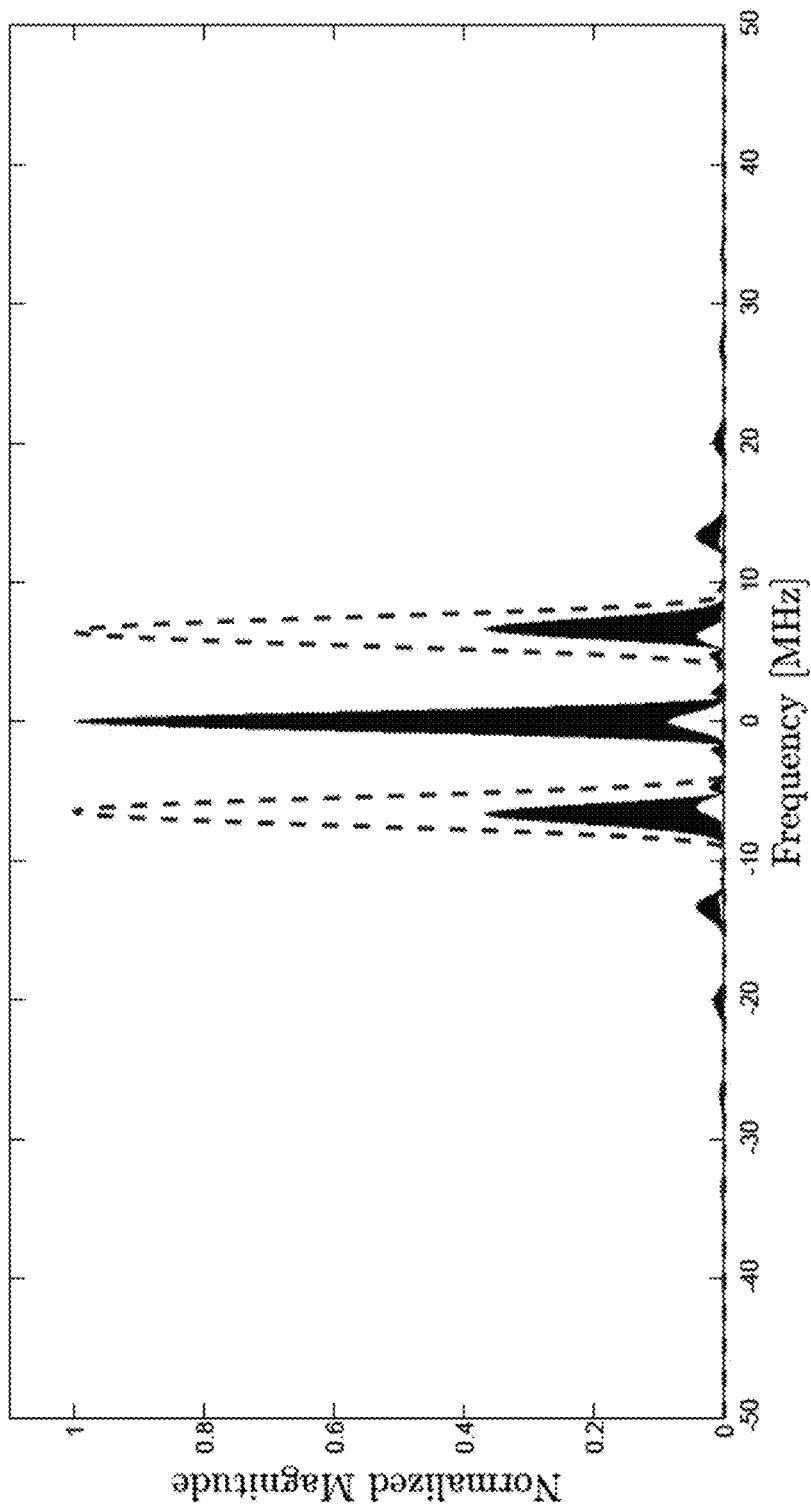
FIG. 6 shows Fourier transforms of the impulse response of a Hanning-based bandpass filter.
Figure 7B:
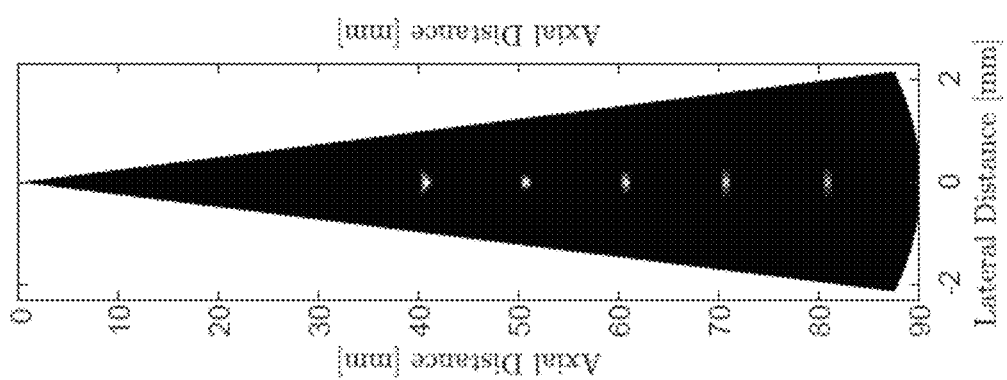
FIGS. 7A-7D show images of simulated point-reflector phantom obtained by DAS and various beamformers, according to several embodiments.
Figure 7A:
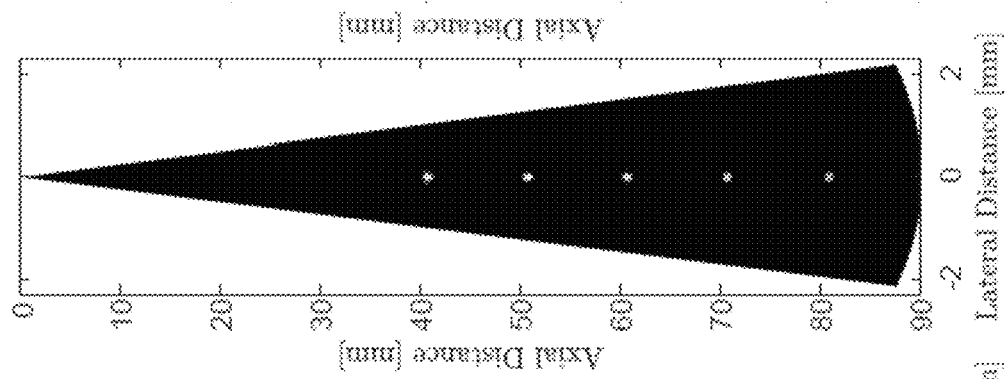
Figure 7D:
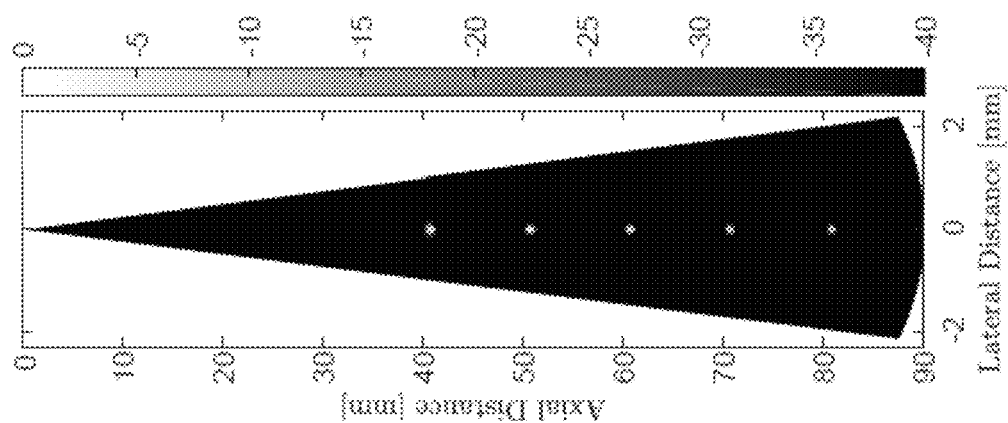
Figure 7C:
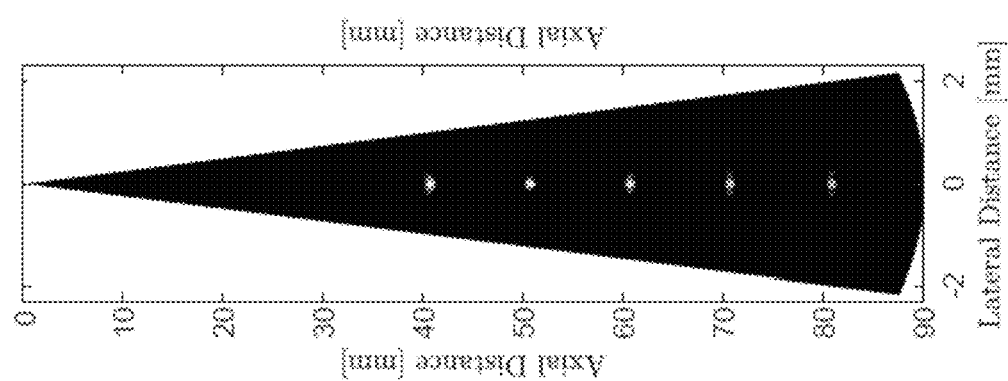

In COBA, SCOBA and SCOBAR, a BP filter was applied using a Hanning window. The window frequency boundaries were empirically determined to well isolate the signal band to be preserved. FIG. 6 shows Fourier transforms of the impulse response of the Hanning-based BP filter (dashed line) and of the signal given by (21), which corresponds to the central simulated image line.

The sampling frequency used is 100 MHz. For SCOBA and SCOBAR, A=B=8 was used, which leads to the minimal numbers of 29 (23%) and 43 (34%) elements respectively, according to Theorem 1 and Theorem 2 above.

Resolution was evaluated using a point-reflector simulated phantom with isolated scatterers distributed in an anechoic background.

FIGS. 7A-7D show, respectively, the results of DAS (127), COBA (127), SCOBA (29), and SCOBAR (43), wherein the number in parenthesis refers to the number of elements used. As seen from the images, SCOBA achieved a comparable lateral resolution to that of DAS while using fewer elements. COBA outperforms DAS in terms of lateral resolution which is seen clearly in the focal depth and beyond it. SCOBAR obtains similar results to COBA using fewer elements.

Figure 8A:
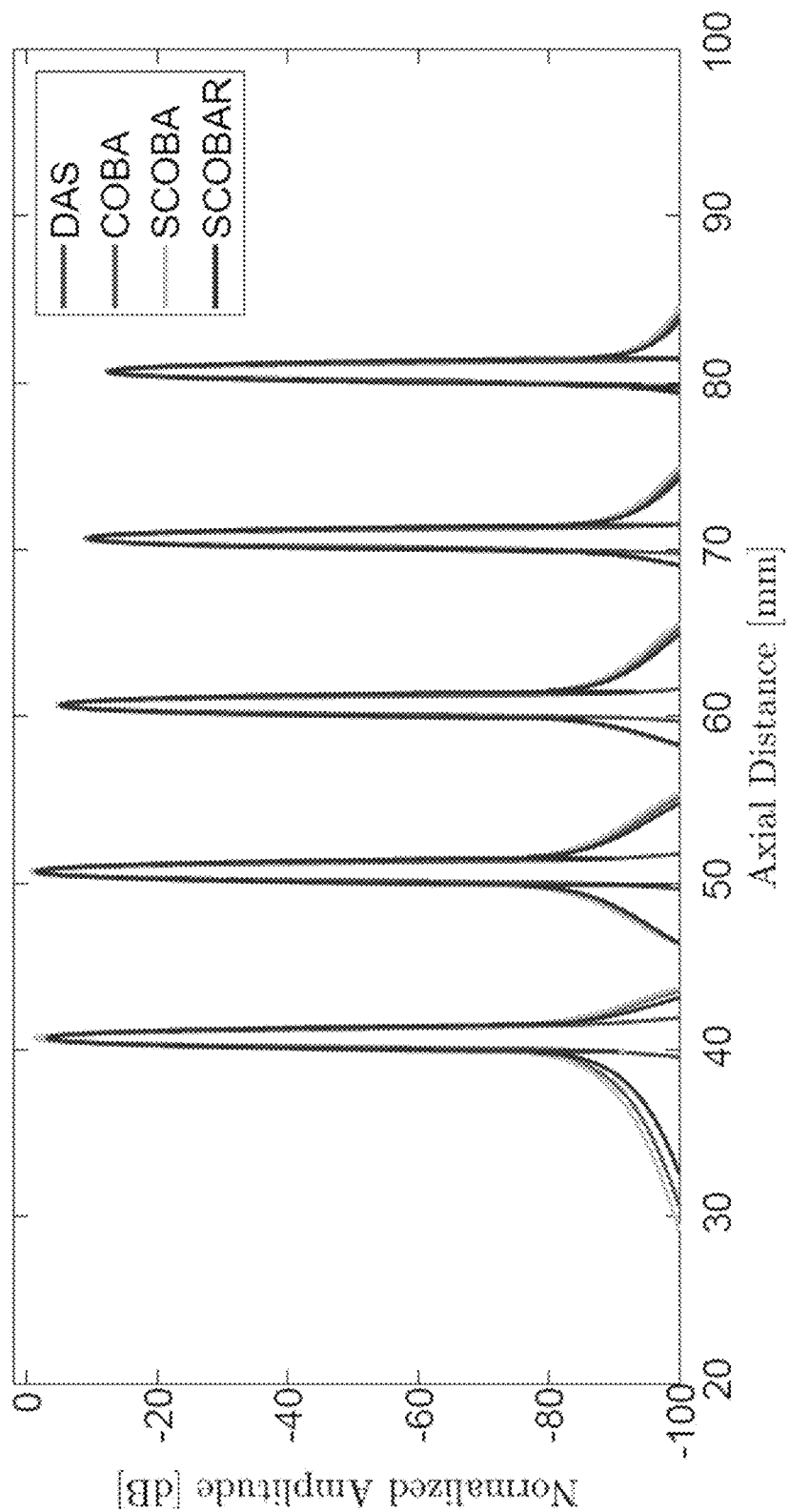
FIGS. 8A-8B show axial profiles and lateral cross sections of DAS and various beamformers, according to several embodiments.
Figure 8B:
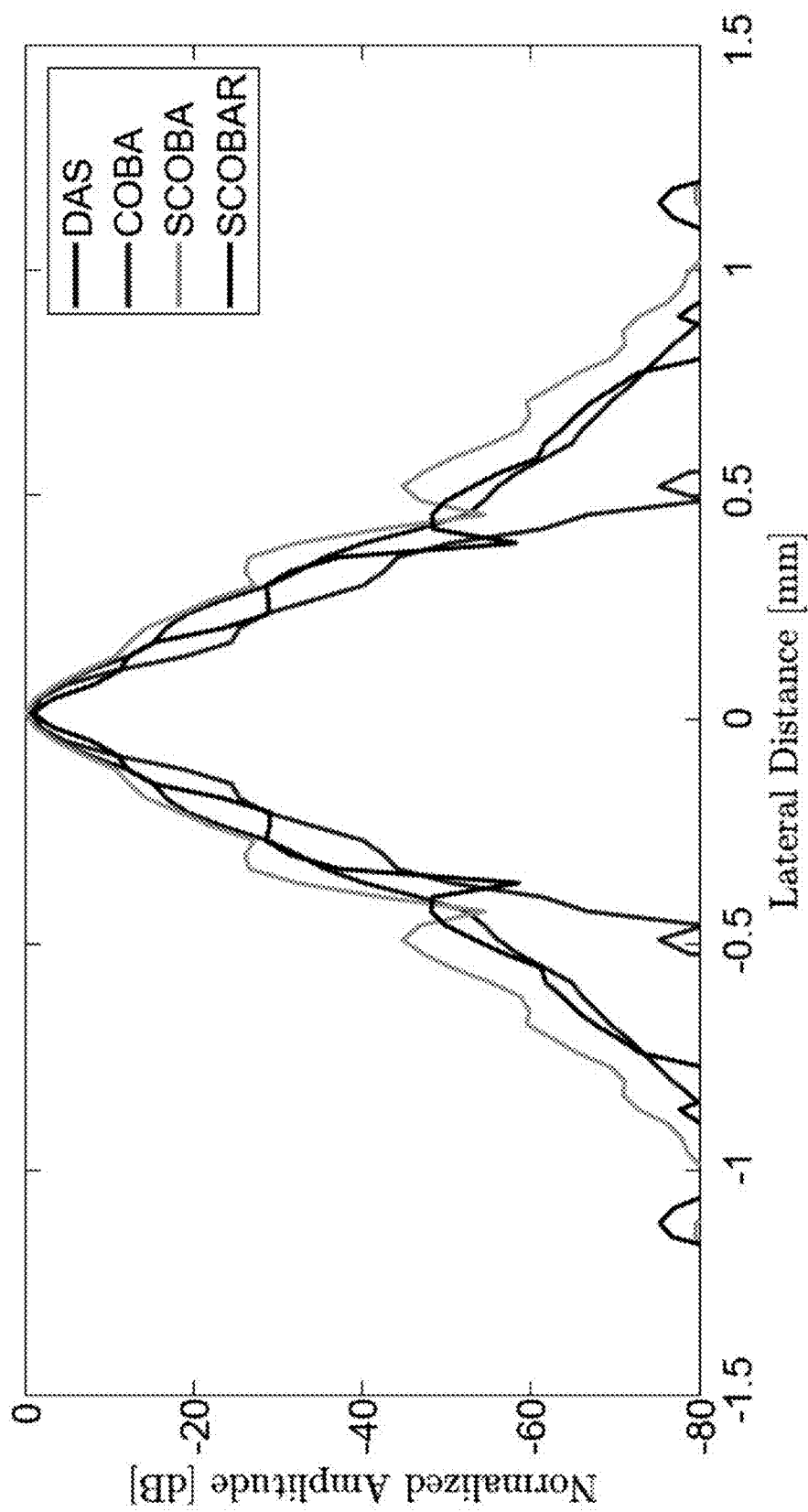
Figure 9B:
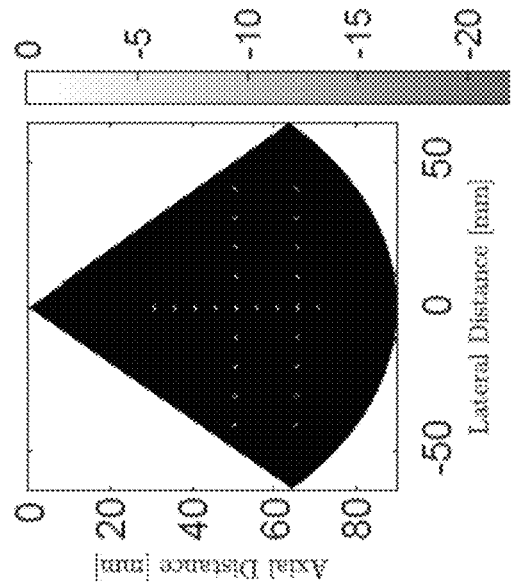
FIGS. 9A-9D show images of simulated on-axis and off-axis point targets obtained by DAS and various beamformers, according to several embodiments.
Figure 9A:
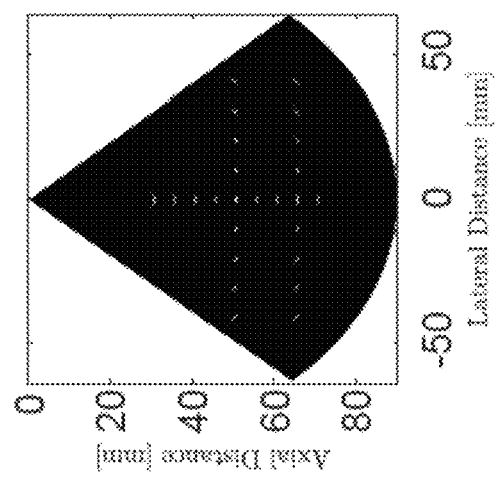
Figure 9D:
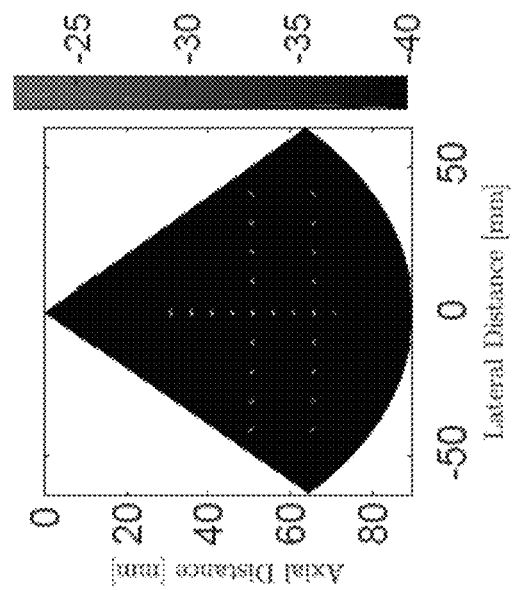
Figure 9C:
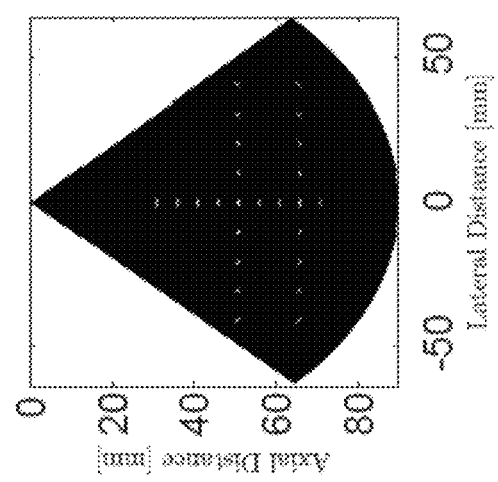

For a closer look, the center image line and the lateral cross-section of the scattering point placed at the transmission focus in 50 mm are shown in FIGS. 8A-8B. One can observe from FIG. 8A that all four methods have similar axial resolution. In terms of lateral resolution, the performance of SCOBA is the same as DAS, while SCOBAR is better than DAS and COBA outperforms them all. FIG. 8B shows lateral cross-sections of all four techniques at focal depth of 50 mm. FIGS. 9A-9D show, respectively, similar on-axis and off-axis point targets obtained by DAS (127), COBA (127), SCOBA (29), and SCOBAR (43), wherein the number in brackets refers to the number of elements used.

Figures 10A, 10B:
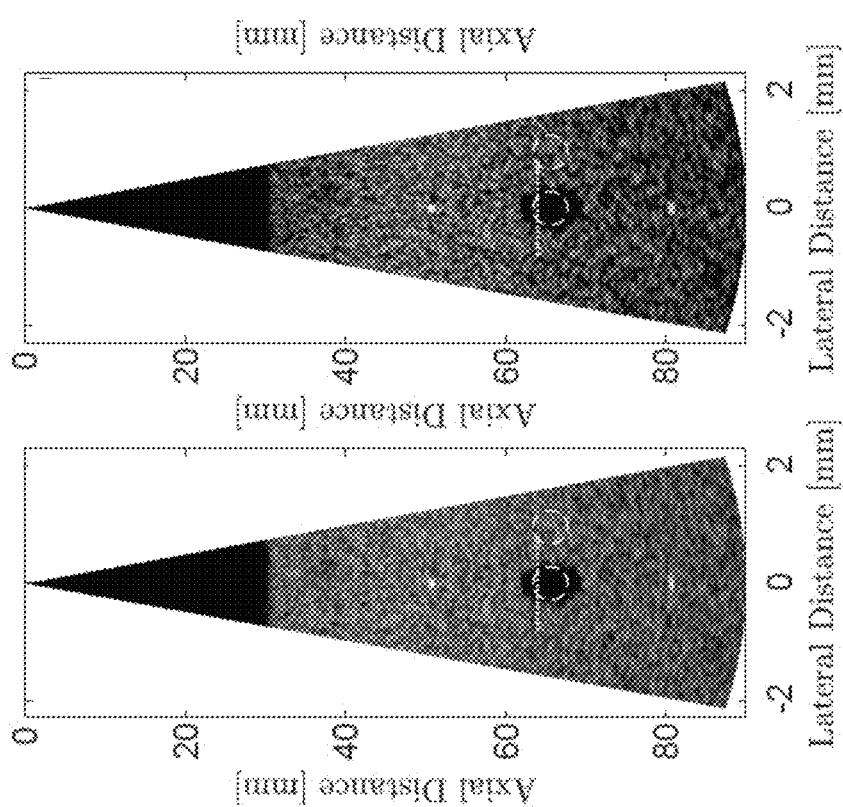
FIGS. 10A-10D show simulation results, according to several embodiments.
Figures 10C, 10D:
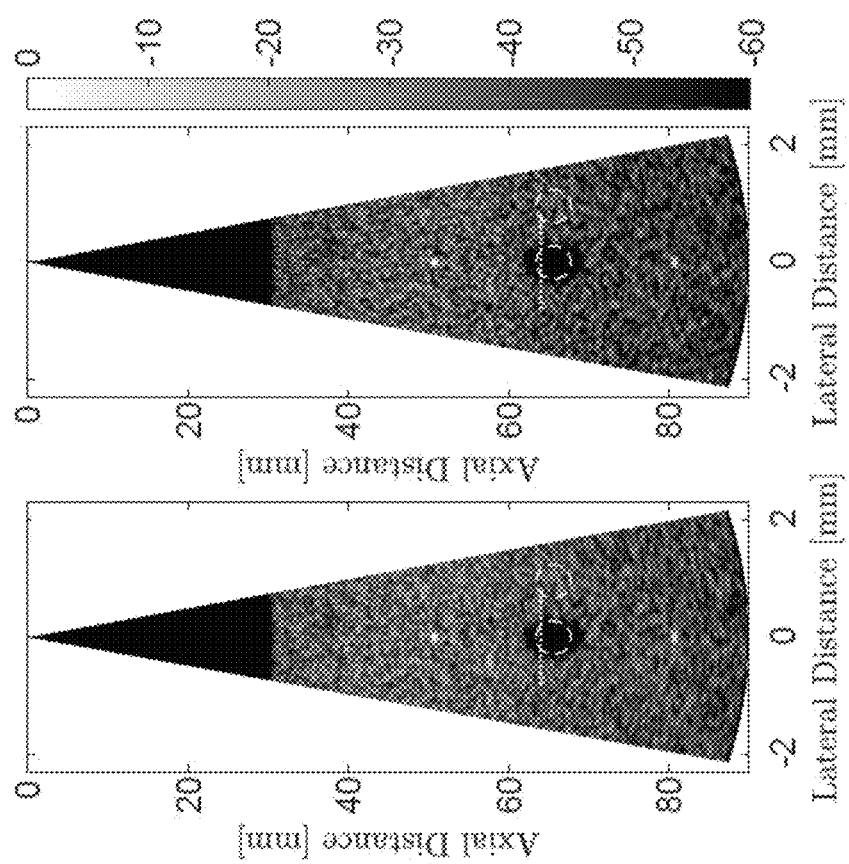
Figure 11:
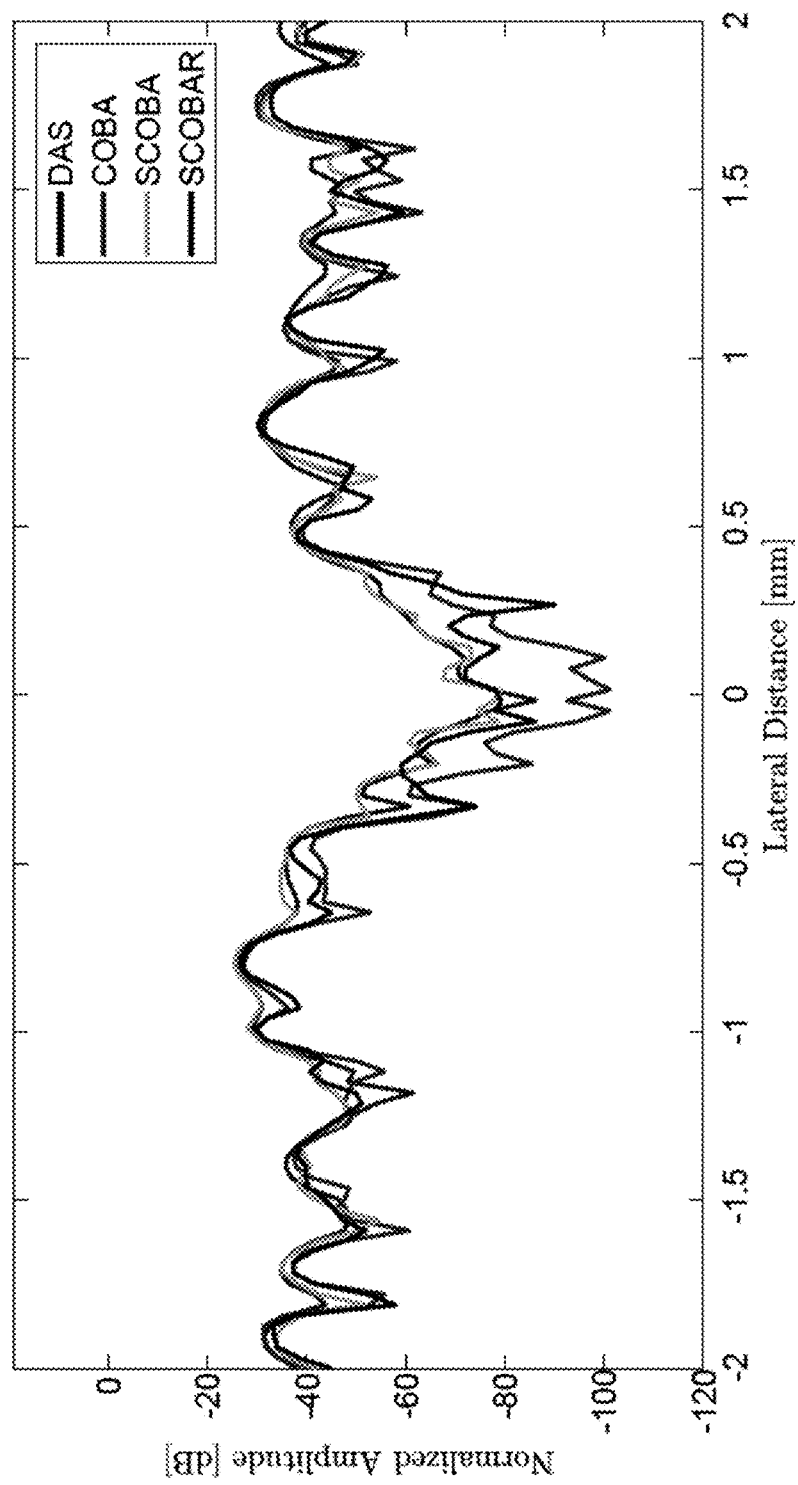
FIG. 11 shows simulation results, according to several embodiments.
Figure 13B:
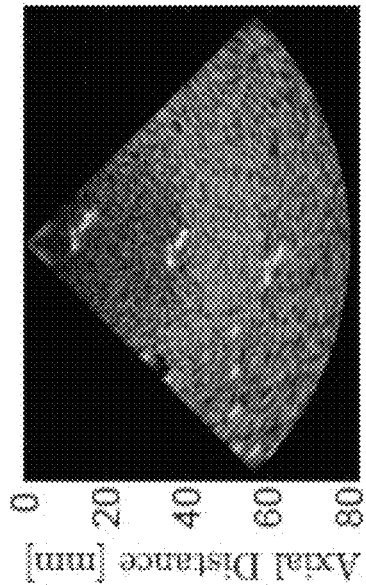
Figure 13A:
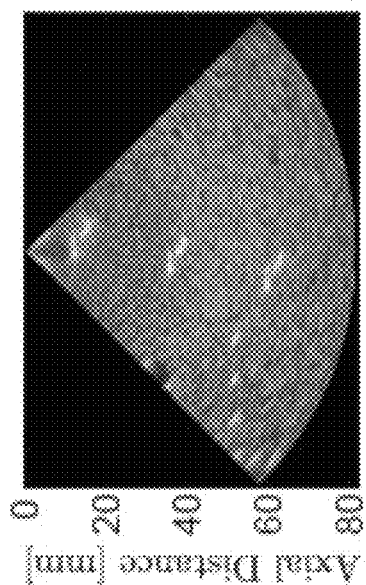
Figure 13D:
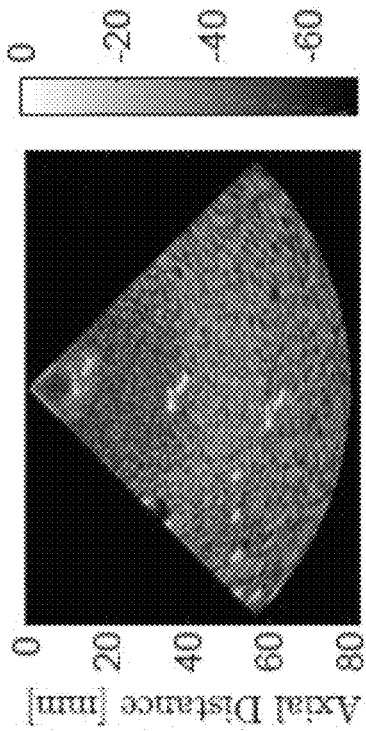
Figure 13C:
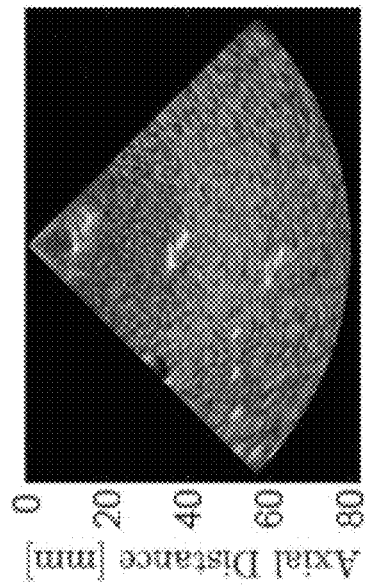

For contrast evaluation, a simulated phantom of an anechoic cyst embedded in a speckle background was used. FIG. 10 displays the images obtained with DAS, COBA, SCOBA and SCOBAR and provides a qualitative impression of the contrast achieved by each method. In addition, lateral cross-sections of the cyst at depth of 64 mm (dashed line in FIG. 10) are presented in FIG. 11, showing that SCOBA and DAS have similar contrast, SCOBAR demonstrates an improvement over the latter and COBA achieves the best performance.

A quantitative measure of contrast is the contrast ratio (CR) [30]

$$CR = 20 \log_{10} \left( \frac{\mu_{cyst}}{\mu_{bck}} \right) \tag{71}$$

where $\mu_{cyst}$ and $\mu_{bck}$ are the mean image intensities, prior to log-compression, computed over small regions inside the cyst and in the surrounding background respectively. The regions selected are designated by a dashed circles in FIG. 10. Consistent with previous results, the CR of DAS is −30.1 dB and of SCOBA is similar and equal to −30 dB. The CR of SCOBAR and COBA are −34 dB and −44 dB, receptively. These results emphasize the superiority of COBA and demonstrate that similar and improved performance to that of DAS can be obtained while using much fewer elements.

Next, the proposed beamformers are evaluated using experimental data. To that end, phantom data was acquired by a Verasonics Vantage 256 system. Tissue mimicking phantoms Gammex 403GSLE and 404GSLE were scanned by a 64-element phased array transducer P4-2v with a frequency response centered at 2.9 MHz and a sampling frequency of 11.9 MHz. The parameters for SCOBA and SCOBAR were chosen to be A=4 and B=8, resulting in 21 and 27 elements respectively. The results obtained from different phantom scans are presented in FIGS. 12A-14D and include on-axis and off-axis targets, various cysts and resolution target groups. Zoom in on areas of cysts and resolution targets are shown in FIGS. 15A-16D, respectively. As can be seen, COBA exhibits an improvement over DAS in terms of contrast and resolution, SCOBA and SCOBAR achieve similar performance to DAS and COBA respectively, while using fewer elements.

Figure 18:
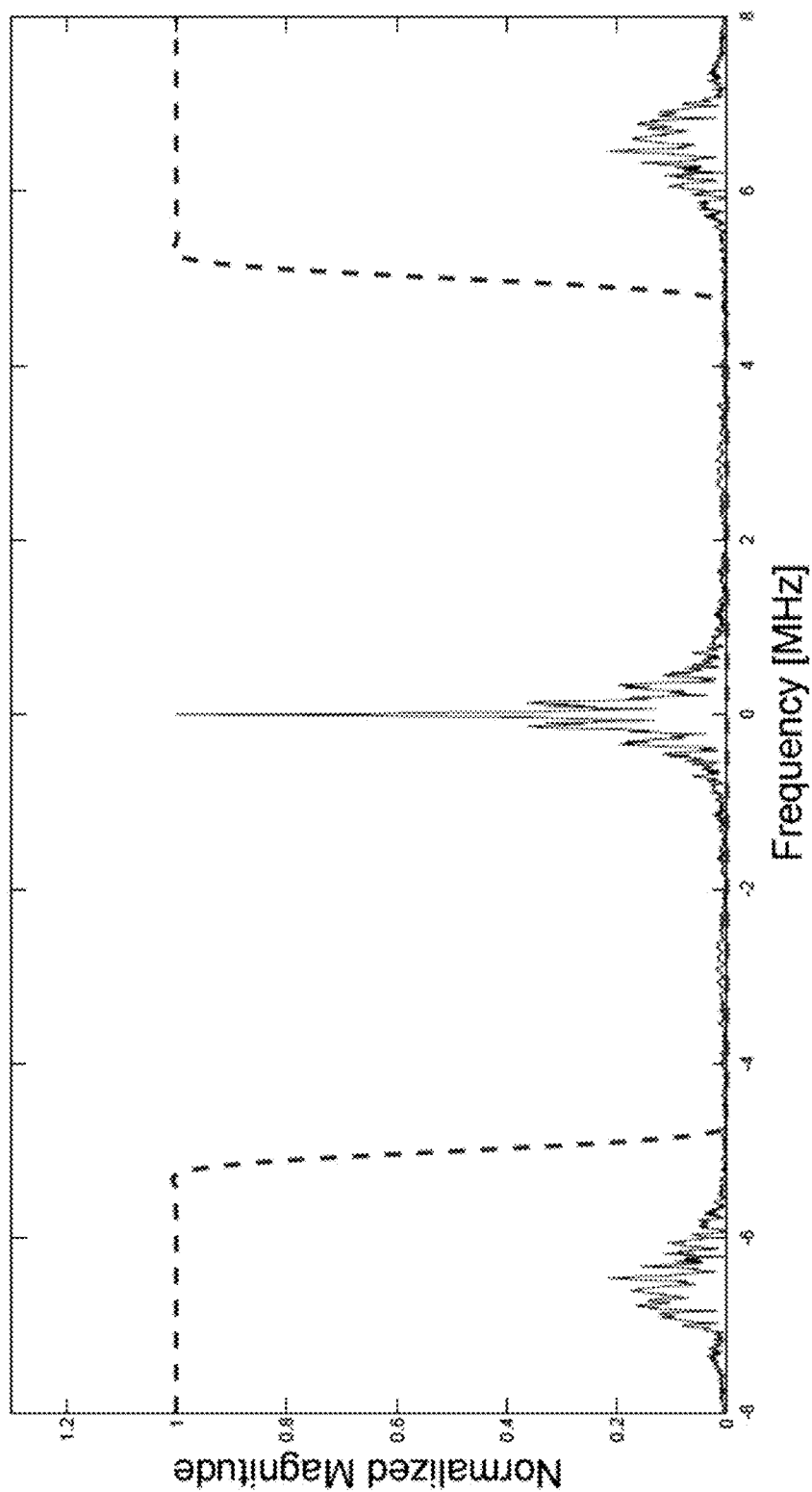

Finally, the proposed methods were applied on in vivo cardiac data. The acquisition was performed with a GE breadboard ultrasonic scanner where 63 acquisition channels were used. The radiated depth was 16 cm, the probe carrier frequency was 3.4 MHz and the system sampling frequency was 16 MHz. For COBA, SCOBA and SCOBAR a Hanning window-based high-pass filter was used (rather than a band-pass) with a cutoff frequency of 5 MHz, as shown in FIG. 18. The parameters for SCOBA and SCOBAR were set to A=4 and B=8, leading to the minimal numbers of elements that can be obtained as stated in Theorems 1 and 2. Consequently, 21 and 27 elements out of 63 were used by SCOBA and SCOBAR respectively.

The results are presented in FIGS. 17A-17D. Clearly, COBA outperforms DAS in terms of image quality; the background noise is reduced and the anatomical structures are better highlighted. SCOBA achieves similar resolution as DAS, whereas, SCOBAR yields notable resolution improvement. Moreover, both the sparse beamformers obtain a low noise floor compared to DAS and thus the heart walls are better defined. These results validate that using the proposed techniques a reduction in the number of elements can be attained without compromising and even improving the image quality in comparison to standard DAS.

What is claimed is:

1. A method of producing an image by at least one processor, the method comprising:
   receiving from a transducer array, having a plurality of transducer elements, a respective plurality of signals comprising reflections of a transmitted signal from a target;
   computing a sub-array U of transducer elements of the transducer array;
   computing a signal vector comprising delayed versions of the plurality of signals of the transducer elements of sub-array U;
   performing a convolution of the signal vector with itself;
   calculating a weighted sum of the results of said convolution, to derive a beamformed signal; and
   reconstructing an image of said target, based on said beamformed signal in real-time,
   wherein the transducer array is a Uniform Linear Array (ULA), and wherein sub-array U is computed such that a sum co-array of sub-array U comprises all transducer elements of the ULA, and
   wherein the transducer array comprises a plurality (2N−1) of transducer elements, wherein N is a product of integers A and B, and wherein the method further comprises:
   calculating a subset $U_A$ of the (2N−1) transducer elements, based on A;
   calculating a subset $U_B$ of the (2N−1) transducer elements, based on A and B; and
   calculating sub-array U as a unification of subsets $U_A$ and $U_B$, having less than (2N−1) transducer elements.

2. The method of claim 1, wherein said transducer is an ultrasound transducer, and wherein said target is a bodily tissue.

3. The method of claim 1, wherein the transducer elements are aligned along a lateral axis, and wherein performing a convolution of the signal vector with itself comprises:
   calculating a square root of each entry of the signal vector; and
   calculating the convolution on the square root values, using Fast Fourier Transform (FFT), to obtain a discrete linear convolution in a direction of the lateral axis.

4. The method of claim 1, wherein said convolution is: (a) a linear convolution in the lateral direction; and (b) based, at least in part, on a Fourier transform.

5. The method of claim 1, wherein calculating said weighted sum comprises adjusting an intrinsic apodization function of said beamformed signal.

6. The method of claim 1, wherein said transducer array comprises a sparse array of transducer elements.

7. A system comprising:
   at least one hardware processor, and a non-transitory computer-readable storage medium having stored thereon program instructions, the program instructions executable by the at least one hardware processor to:
   receive from a transducer array, having a plurality of transducer elements, a respective plurality of signals comprising reflections of a transmitted signal from a target;
   compute a sub-array U of transducer elements of the transducer array; compute a signal vector comprising delayed versions of the plurality of signals of the transducer elements of sub-array U;
   perform a convolution of the signal vector with itself;
   calculating a weighted sum of the results of said convolution, to derive a beamformed signal; and
   reconstruct an image of said target, based on said beamformed signal, in real-time,
   wherein the transducer array is a Uniform Linear Array (ULA), and wherein sub-array U is computed such that a sum co-array of sub-array U comprises all transducer elements of the ULA,
   wherein the transducer array comprises a plurality (2N−1) of transducer elements, wherein N is a product of integers A and B, and wherein the hardware processor is further configured to:
   calculate a subset $U_A$ of the (2N−1) transducer elements, based on A;
   calculate a subset $U_B$ of the (2N−1) transducer elements, based on A and B; and
   calculate sub-array U as a unification of subsets $U_A$ and $U_B$, having less than (2N−1) transducer elements.

8. The system of claim 7, wherein said convolution is: (a) a linear convolution in the lateral direction; and (b) performed in real-time based, at least in part, on an FFT transform.

9. The system of claim 7, wherein calculating said weighted sum comprises adjusting an intrinsic apodization function of said beamformed signal.

10. The method of claim 1 wherein reconstructing an image of said target comprises:
    applying a band-pass filter, centered about a harmonic frequency of the transducer on the beamformed signal; and
    reconstructing the image based on the filtered beamformed signal.

11. The method of claim 1, wherein reconstructing an image of said target further comprises applying a temporal filter on each signal of said plurality of signals, to steer the beamformed signal towards desired directions in space, thus creating a line in the image.

12. The method of claim 1, further comprising:
    constructing a strict sub-array of the array of transducer elements; and
    deriving the beamformed signal, based on the received signals of the strict sub-array.

13. The method of claim 1, wherein the plurality (2N−1) of transducer elements are indexed as $\{-(N-1), \ldots, 0, \ldots, (N-1)\}$ of the ULA, and wherein subset $U_A$ comprises transducer elements of indices $\{-(A-1), \ldots, 0, \ldots, (A-1)\}$ of the ULA, and wherein subset $U_B$ comprises transducer elements of indices $\{n \cdot A | n = -(B-1), \ldots, 0, \ldots, (B-1)\}$ of the ULA.

14. A method of producing an image by at least one processor, the method comprising:

receiving from a transducer array, having a plurality of transducer elements, a respective plurality of signals comprising reflections of a transmitted signal from a target;

computing a sub-array U of transducer elements of the transducer array;

computing a signal vector comprising delayed versions of the plurality of signals of the transducer elements of sub-array U;

performing a convolution of the signal vector with itself;

calculating a weighted sum of the results of said convolution, to derive a beamformed signal; and reconstructing an image of said target, based on said beamformed signal in real-time, wherein the transducer array is a Uniform Linear Array (ULA), and wherein sub-array U is computed such that a sum co-array of sub-array U comprises all transducer elements of the ULA, and wherein the transducer array comprises a plurality (2N) of transducer elements, wherein N is a product of integers A and B, and wherein selecting sub array U comprises:

calculating a subset $U_A$ of the (2N) transducer elements, based on A;

calculating a subset $U_B$ of the (2N) transducer elements, based on A and B; and calculating sub-array U as a unification of subsets $U_A$ and $U_B$, having less than (2N) transducer elements.

15. The method of claim 14, wherein the plurality (2N) of transducer elements are indexed as $\{-(N-1), \ldots, 0, \ldots, (N)\}$ of the ULA, and wherein subset $U_A$ comprises transducer elements of indices $\{-(A-1), \ldots, 0, \ldots, (A-1)\}$ of the ULA, and wherein subset $U_B$ comprises transducer elements of indices $\{n \cdot A | n = -(B-1), \ldots, 0, \ldots, (B-1)\}$ of the ULA.

16. The method of claim 1, wherein the sub array U comprises the same number of transducer elements as the transducer array, and wherein the reconstructed image is characterized by improved resolution, in relation to delay and sum (DAS) beamforming with the same number of transducer elements.

* * * * *